United States Patent [19]
Wheeler et al.

[11] Patent Number: 5,565,232
[45] Date of Patent: *Oct. 15, 1996

[54] REDUCED CALORIE TRIGLYCERIDE MIXTURES

[75] Inventors: Edward L. Wheeler, Fairfield, N.J.;
Ronald P. D'Amelia, Hicksville, N.Y.;
Gilbert A. Leveilla, Denville, N.J.;
Michael S. Otterburn, Randolph, N.J.;
Lawrence P. Klemann, Somerville,
N.J.; John W. Finley, Whippany, N.J.;
Allan D. Roden, Nobelsville, Ind.;
Michael M. Chrysam, Blairstown,
N.J.; Turiddu A. Pelloso, Carmel, Ind.;
Peter S. Given, Jr., Glencoe, Ill.

[73] Assignee: Nabisco, Inc., Parsippany, N.J.

[*] Notice: The term of this patent shall not extend beyond the expiration date of Pat. No. 5,258,197.

[21] Appl. No.: 477,009

[22] Filed: Jun. 7, 1995

Related U.S. Application Data

[60] Continuation of Ser. No. 175,020, Dec. 29, 1993, Pat. No. 5,456,939, which is a division of Ser. No. 83,795, Jun. 28, 1993, Pat. No. 5,378,490, which is a division of Ser. No. 804,140, Dec. 6, 1991, Pat. No. 5,258,197, which is a continuation-in-part of Ser. No. 624,056, Dec. 7, 1990, abandoned, and Ser. No. 410,161, Sep. 20, 1989, abandoned, and Ser. No. 655,629, Mar. 6, 1991, abandoned, and Ser. No. 732,518, Jul. 19, 1991, abandoned.

[51] Int. Cl.$^6$ ..................................... A23G 1/00
[52] U.S. Cl. .................. 426/607; 426/660; 426/804
[58] Field of Search ................................... 426/607, 660, 426/804, 601

[56] References Cited

U.S. PATENT DOCUMENTS

| | | |
|---|---|---|
| 2,614,937 | 10/1952 | Baur et al. |
| 2,615,159 | 10/1952 | Jackson |
| 2,615,160 | 10/1952 | Baur |
| 3,192,057 | 6/1965 | Hines et al. |
| 3,388,085 | 6/1968 | Levkoff et al. |
| 4,272,548 | 6/1981 | Gatzen et al. |
| 4,364,868 | 12/1982 | Hargreaves |
| 4,390,561 | 6/1983 | Blair et al. |
| 4,447,462 | 5/1984 | Tafuri et al. |
| 4,479,976 | 10/1984 | Lansbergen et al. |
| 4,486,457 | 12/1984 | Schijf et al. |
| 4,504,503 | 3/1985 | Biernoth et al. |
| 4,832,975 | 5/1989 | Yang |
| 4,839,192 | 6/1989 | Sagi et al. |
| 4,865,866 | 9/1989 | Moore |
| 4,873,109 | 10/1989 | Tanaka et al. |
| 4,883,684 | 11/1989 | Yang |
| 5,258,197 | 11/1993 | Wheeler ............... 426/607 |
| 5,407,695 | 4/1995 | Wheeler ............... 426/607 |
| 5,411,754 | 5/1995 | Wheeler ............... 426/607 |

FOREIGN PATENT DOCUMENTS

| | | |
|---|---|---|
| 322027 | 12/1988 | European Pat. Off. |
| 64-19042 | 1/1989 | Japan |
| 2-158695 | 6/1990 | Japan |
| 822730 | 2/1956 | United Kingdom |
| 816343 | 4/1956 | United Kingdom |

OTHER PUBLICATIONS

Akoh, C. C. and Swanson, B. G., J. Amer. Oil Chem. Soc. 66: 1581–1587 (1989).
Ambrose, A. M. and Robbins, D. J., J. Nutr. 58: 113–124 (1956).
Babayan, V. K., Beare–Rogers, J., Ed., Dietary Fat Requirements in Health and Development, A.O.C.S. 1988, Chapter 5, pp. 73–86.
Bailey's Industrial Oil and Fat Products, 4th Ed., J. Wiley, New York, 1979, vol. 1, pp. 16 to 17.
Baur, F. J., J. Amer. Oil Chem. Soc. 31: 147–151 (1954).
Carroll, K. K., J. Nutr. 64: 399–410 (1957) at 408.
Clement, G., et al., Biochem. Biophys. Res. Commun. 8: 238–242 (1962).
Coleman, R. D., et al., J. Amer. Oil Chem. Soc. 40: 737–742 (1963).
Cummings, J. H., Gut 22: 763–779 (1981).
Desnuelle, P. and Savary, P., J. Lipid Res. 4:369–384 (1963).
Deuel, H. J., The Lipids, vol. II, Interscience Publishers, 1955, pp. 218–227.
Eckstein, J. Biol. Chem. 81: 613–628 (1929) at 622.
Feuge, R. O., Food Technology 9: 314–318 (1955).
Hashim, S. A. and Babayan, V. K., Am. J. Clin. Nutr. 31: S273–276 (1978).
Holt, L. E., et al., J. Ped. 6: 427–480 (1935) Table VIII, p. 445, and Conclusions, No. 4, p. 477.
Jackson, F. L., et al., J. Amer. Chem. Soc. 73: 4280–4284 (1951).
Jackson, F. L., and Lutton, E. S., J. Amer. Chem. Soc. 74: 4827–4829 (1952).
Kaunitz, et al., J. Amer. Oil Chem. Soc. 35: 10–13 (1957).
Lovegren, N. V., and Gray M. S., J. Amer. Oil Chem. Soc. 55: 310–316 (1978).
Mattson, F., et al., J. Nutr. 109: 1682–1687 (1979).
Mattson, F. H., J. Nutr. 69: 338–342 (1959).
Mattson, F. H., et al., J. Nutr. 59: 277–285 (1956).
McAtee, J. W., et al., Life Sci. 7: 769–775 (1968).
Mead, J., et al. Lipids, Plenum, New York, 1986, pp. 459–470.
Mensink, R. P. and Katan, M. B., New Eng. Jour. Med., 323: 439–445 (1990).

(List continued on next page.)

*Primary Examiner*—Carolyn Paden

[57] ABSTRACT

Fat mixtures enriched with triglycerides having long, saturated, preferably $C_{16}$ to $C_{22}$, fatty acid residues and short, preferably $C_2$ to $C_4$, acid residues are employed in edible compositions as low calorie fats. The preferred embodiments comprise mixtures of at least two triglycerides bearing long residues (e.g. stearyl) and short residues (e.g. acetyl or propyl). In one preferred embodiment, each triglyceride contains short chain residues which are different from those in the other triglyceride. In another preferred embodiment, at least a portion of the triglycerides have two different short residues. Methods of using the low calorie fats and food products incorporating them, particularly in coating, shortening and margarine products, are disclosed.

4 Claims, 4 Drawing Sheets

OTHER PUBLICATIONS

Ozaki, J., Biochem. Z. 177: 156–167 (1926), Full German Text and translation of pp. 156 to 163.

Ravin, H. A. and Seligman, A. M., Arch. Biochem. Biophys. 42: 337–354 (1953) at 353.

Schonheyder, F. and Volqvartz, K., Enzymologia 11: 178–185 (1943).

Snyderman, S. E., et al., Arch. Dis. Childhood 30: 83–84 (1955).

Sobotka, H. and Glick, D., J. Biol. Chem. 105: 199–219 (1934).

Tomarelli, et al., J. Nutr. 95: 583–590 (1968).

Wang, C. S., et al., J. Biol. Chem. 258: 9197–9202 (1983).

Weinstein, S. S. and Wynne, A. M., J. Biol. Chem. 112: 641–649 (1936).

Wills, E. D., in Desnuelle, P. Ed., The Enzymes of Lipid Metabolism, Pergamon Press, N.Y., 1961, pp. 13 to 19.

REDUCED CALORIE TRIGLYCERIDE MIXTURES

RELATED U.S. APPLICATION DATA

This is a continuation of Ser. No. 08/175,020 filed Dec. 29, 1993, now U.S. Pat. No. 5,456,939, which is a divisional application of Ser. No. 08/083,795 filed on Jun. 28, 1993, now U.S. Pat. No. 5,378,490 which is a divisional application of Ser. No. 07/804,140 filed Dec. 6, 1991, now U.S. Pat. No. 5,258,197 which is a continuation-in-part of Ser. No. 07/624,056 filed Dec. 7, 1990, now abandoned, and a continuation-in-part of Ser. No. 07/410,161 filed Sep. 20, 1989, now abandoned, and also a continuation-in-part of 07/665,629 filed Mar. 6, 1991 now abandoned and a continuation-in-part of 07/732,518 filed Jul. 19, 1991 now abandoned.

TECHNICAL FIELD

This invention relates to the use of low calorie triglyceride mixtures in edible compositions.

Dietary fat is the most concentrated source of energy of all the nutrients, supplying 9 kcal/gram, about double that contributed by either carbohydrate or protein. The amount of fat in the American diet has increased in the last 60 years by about 25% (Mead, J., et al. Lipids, Plenum, New York, 1986, page 459), so that fats now provide approximately 40% (or more) of the daily caloric intake.

Fat contributes to the palatability and flavor of food, since most food flavors are fat-soluble, and to the satiety value, since fatty foods remain in the stomach for longer periods of time than do foods containing protein and carbohydrate. Furthermore, fat is a carrier of the fat-soluble vitamins, A, D, E, and K, and the essential fatty acids, which have been shown to be important in growth and in the maintenance of many body functions. Hence, major research efforts have focused on ways to produce food substances that provide the same functional and organoleptic properties as fats, but not the calories. Synthetic fats have been created and are now undergoing testing for safety. Unfortunately, many consumers are concerned with the synthetic connotation of food additives of this type and will not avail themselves of the advantages they offer.

There is a need for a fat which is low in calories and high in functionality, but is not perceived as artificial.

BACKGROUND ART

The most abundant group of fats are triglycerides—esters of fatty acids with glycerol (1,2,3-propanetriol). Natural fats have a broad range of functionalties and are handled in different ways by the human digestive process.

Early studies reported that triglyceride fats having high melting points were less digestible (Deuel, H. J., The Lipids, vol. II, Interscience Publishers, 1955, pages 218 to 220). Later investigators questioned the relationship between digestibility and melting points, and scrutinized instead the chain lengths and degree of unsaturation of fatty acid substituents; straight chain, saturated fatty acids having 4 up to 10 carbon atons were completely digested by rats, those having 10 to 18 carbons progressively less digested, and those having 18 or higher only slightly absorbed, while monounsaturated acids were about the same as saturated acids having 6 carbons (Carroll, K. K., J. Nutr. 64: 399–410 (1957) at 408).

In other triglyceride metabolic studies in man only limited areas of predictability could be found. In one study a coconut oil fraction containing predominantly saturated, long chain triglycerides bearing 89% stearic ($C_{18}$) and 11% palmitic ($C_{16}$) acid residues were absorbed 31%, compared to 98% for corn oil (Hashim, S. A., and Babayan, V. K., Am. J. Clin. Nutr. 31: S273–276 (1978)). However, it was found that increasing the stearic acid content of dietary fat did not per se decrease absorbability; rather, absorbability could be decreased by increasing the amount of tristearin present (i.e., triglycerides having three stearic residues; see Mattson, F.H., J. Nutr. 69: 338–342 (1959)). To this observation were added the findings that, in the presence or absence of dietary calcium and magnesium, stearic acid was well absorbed by rats when esterified on the 2-position of triglycerides having oleic acid at the 1- and 3-positions, but absorption decreased when a second stearic was added to the 1-position (Mattson, F., et al., J. Nutr. 109: 1682–1687 (1979), Table 3, page 1685). Stearic acid in the 1-position was well absorbed from triglycerides having oleic in the 2- and 3-positions in the absence, but not in the presence, of dietary calcium and magnesium (ibid.). When stearic was in both the 1- and 3-positions, absorption decreased with or without dietary calcium and magnesium, but the effect was more pronounced when calcium and magnesium were sufficient (ibid.).

The digestibility of palmitic acid has also been studied. Palmitic acid was better absorbed by rats when situated at the 2-positions of triglycerides than at the 1- or 3-positions in naturally occurring fats commonly fed to infants, and total fat absorption was adversely influenced by increasing the palmitic and stearic acid content in the 1- and 3-positions (Tomerelli, et al., J. Nutr. 95: 583–590 (1968)).

While triglycerides high in stearic acid are less well utilized than others, they also tend to be high melting. Tristearin is a solid at room temperature; the alpha form is a white powder that melts at 55° C., which, on solidification, reverts to the beta form that melts again at 72° C. The melting points of 1,3-distearin with short or medium chain fatty acids at the 2-position are high (Lovegren, N. V., and Gray, M. S., J. Amer. Oil Chem. Soc. 55: 310–316 (1978)). Symmetrical disaturated triglycerides of stoario acid and/or palmitic, often with oleic at the 2-position, melt fairly uniformly near body temperature, and this property is of advantage for cocoa butter and hard butter substitutes (see, for example, U.S. Pat. No. 4,364,868 to Hargreaves, U.S. Pat. No. 4,839,192 to Sagi, et al., and U.S. Pat. No. 4,873,109 to Tanaka, et al.), and for hardstocks for margarines and shortenings (see, for example, U.S. Pat. No. 4,390,561 to Blair, et al., U.S. Pat. No. 4,447,462 to Tafuri and Tao, U.S. Pat. No. 4,486,457 to Schijf, etal., U.S. Pat. No. 4,865,866 to Moore, and U.S. Pat. No. 4,883,684 to Yang). Because of their functionality, high melting, high stearic fats have limited applications in food compositions requiring more plastic or liquid triglycerides.

Fats have been prepared by substituting acetic acid for a portion of the fatty acids occurring in ordinary fats or oils, thus producing triglycerides bearing short acetyl and long substituents. For saturated fats high in stearic acid, the substitution of acetyl groups for a portion of the stearyl groups lowers the melting point. These acetoglycerides were investigated during the 1950's and found to be digestible. Feeding studies indicated that the nutritive value of mono- and diacetin fats were essentially the same to animals as those fed the corresponding conventional triglycerides (Mattson, F. H., et al., J. Nutr. 59: 277–285 (1956), although acetooleins were more digestible than acetostearins (Ambrose, A. M., and Robbins, D. J., *J. Nutr.* 58: 113–124 (1956) and animals grew poorly when fed acetostearin as the sole dietary fat (Coleman, R. D., et al., *J. Amer. Oil Chem. Soc.* 40: 737–742 (1963)).

While lower melting than tristearin, acetostearins still have high melting points, limiting applications in food products requiring plastic or liquid fats. In fact, though melting points of compounds structurally related generally decrease with decreasing molecular weight (and mono- and distearins having medium to long saturated substituents follow this rule), the melting points of triglycerides in the $C_{18}C_nC_{18}$ and $C_nC_nC_{18}$ series, where n=2 to 6, anomalously show the high molecular weight $C_6$ (caproic acid) mono- and distearin derivatives to have the lowest melting points and the low molecular weight $C_2$ (acetic acid) mono- and distearin derivatives to have the highest (Jackson, F. L., et al., *J. Amer. Chem. Soc.* 73: 4280–4284 (1951) and Jackson, F. L., and Lutton, E. S., *J. Amer. Chem. Soc.* 74: 4827–4829 (1952); see also the data in Example 38). Plastic fats containing acetostearins suggested for use as shortenings and the like were formulated to contain significant levels of unsaturated fats and typically employed significant levels of fatty acids which would yield high saponification numbers or were liquid at room temperature (U.S. Pat. No. 2,6714,937 to Baur and Lange (1952) and Baur, F. J., *J. Amer. Oil Chem. Soc.* 31: 147–151 (1954)).

Acetostearins are waxy fats having sharp melting points. In contrast to fats bearing medium and/or long substituents, acetostearins also exhibit unusual polymorphism (ibid., and Feuge, R. O., *Food Technology* 9: 314–318 (1955)). Because of their melting and crystal properties, the fats have been suggested as useful for coating food products such as meat, fish, cheese, and candy (U.S. Pat. Nos. 2,615,159 to Jackson and 2,615,160 to Baur). Compositions of this nature are often referred to as "hot melts" and may contain antibiotics (U.S. Pat. No. 3,192,057 to Hines and Shirk) or polymeric materials (U.S. Pat. No. 3,388,085 to Levkoff and Phillips) to to prolong the life of the coating.

The short chain fatty acids, acetic, propionic, and burytic acid, also called, as a group, volatile fatty acids, occur in the large intestine of all mammalian species so far studied (Cummings, J. H., *Gut* 22: 763–779 (1981)). Except for a small percentage of butyric acid in milk fat (i.e., about 3.5 to 4%), volatile fatty acids rarely occur in nature esterified to glycerol in fats, but are, instead, generally free by-products of fermentation in the gut. Physically, short chain fatty acids "are not at all 'fatlike' in character; in fact they are hydrophilic substances with complete miscibility with water" (*Bailey's Industrial Oil and Fat Products*, 4th. ed., J. Wiley, New York, 1979, volume 1, pages 16 to 17).

Early reports investigating the metabolism of short acids and triglycerides bearing short chain residues showed no regular relationship between nutritional value and the number of carbon atoms in the fat (Ozaki, J., *Biochem. Z.* 177: 156–167 (1926) at 163). For example, when fed to rats at levels of 5% and 10% of the diet, triacetin and tributyrin were nutritious, yielding weight gains in the top 20 to 25% of the fats tested, whereas tripropionin and triisovalerin were toxic (ibid.). In 1929, Eckstein reported that rats fed trioloin and sodium butyrate grew at the same rate (*J. Biol. Chem.* 81: 163–628 (1929) at 622).

In 1935, L. E. Holt, et al., observed that infants fed milk enriched with tributyrin retained more fat per day (90.1 to 90.2%) than those in a butterfat control group (88.9%); the study concluded that absorption was favored by fatty acids with relatively short chains (*J. Ped.* 6: 427–480 (1935), Table VIII, page 445, and Conclusions, number 4, page 477). Similar results were obtained with triacetin, with absorption of tributyrin and triacetin reportedly superior to that of corn oil, although corn oil yielded higher calories (Snyderman, S. E., et al., *Arch. Dis. Childhood* 30: 83–84 (1955)). Substitution of triacetin, tripropionin, or tributyrin for half the glucose and starch in a rat diet did not significantly affect the digestible, metabolizable or net energy measurements, but lower body weight gains were observed in animals fed tributyrin in two experiments and triacetin in one experiment (McAtee, J. W., et al., *Life Sci.* 7: 769–775 (1968)).

In in vitro digestibility studies, tributyrin is readily cleaved by pancreatic lipase. Data measuring lipolysis as a function of chain length show tributyrin much more rapidly hydrolyzed than other substrates (see Sobotka, H., and Glick, D., *J. Biol. Chem.* 105: 199–219 (1934), comparing triglycerides bearing three identical $C_4$ to $C_{18}$ acyl groups, and Desnuelle, P., and Savary, P., *J. Lipid Res.* 4: 369–384 (1963), comparing triglycerides bearing three identical $C_2$ to $C_{18}$ acyl groups), although some reports rank tripropionin slightly better (Weinstein, S. S., and Wynne, A. M., *J. Biol. Chem.* 112: 641–649 (1936), comparing triglycerides bearing three identical $C_2$ to $C_6$ acyl groups, and Wills, E. D., in Desnuelle, P., ed., *The Enzymes of Lipid Metabolism*, Pergamon Press, New York, 1961, pages 13 to 19, comparing triglycerides bearing three identical $C_2$ to $C_{18}$ acyl groups). In fact, because tributyrin is such a good substrate and because the triglyceride is sufficiently water-soluble to allow enzymatic measurements in a homogeneous solution, it is often selected as a lipase substrate standard (Ravin, H. A., and Seligman, A. M., *Arch. Biochem. Biophys.* 42: 337–354 (1953) at 353).

Other lipase preparations readily cleave short chain triglycerides. Tributyrin was found to be hydrolyzed with the greatest initial velocity by human milk lipase, while pig liver lipase hydrolyzed tripropionin and tributyrin with an equal initial velocity much greater than any other in a study comparing $C_2$ to $C_{18}$ triglycerides (Schonheyder, F., and Volqvartz, K., *Enzymologia* 11: 178–185 (1943)). Tributyrin was hydrolyzed more readily than $C_6$ to $C_{18}$ triglycerides by human milk bile salt-activated lipase (Wang, C. S., etal., *J. Biol. Chem.* 258: 9197–9202 (1983)). A liver lipase hydrolyzed trivalerin the fastest, with tributyrin the second fastest (Sobotka and Glick, cited above).

In contrast to triglycerides bearing long chain (~$C_{16}$ to $C_{24}$) fatty acids and those bearing short chain fatty acids, medium chain triglycerides, generally obtained from kernel oils or lauric fats and encompassing those substituted with $C_6$ to $C_{12}$, predominantly $C_8$ to $C_{10}$, fatty acids, have been of particular interest because they are more rapidly absorbed and metabolized, via a different catabolic route than those bearing long chain fatty acids (see a recent review by Babayan, V. K., in Beare-Rogers, J., ed., *Dietary Fat Requirements in Health and Development*, A.O.C.S. 1988, chapter 5, pages 73 to 86). Hence, medium chain triglycerides have been employed in premature infant formulas and in the treatment of several malabsorption syndromes (ibid.). Feeding studies by H. Kaunitz, et al., demonstrated the usefulness of medium chain triglycerides in weight maintentance and obesity control in rats (*J. Amer. Oil Chem. Soc.* 35: 10–13 (1957)).

Several research groups have exploited the physical and nutritional properties of medium chain fatty acids by suggesting that triglycerides having stearic and/or behenic acid in combination with medium chain substituents be used as low calorie fats (Eur. Pat. Ap. Pub. No. 322,027, corresponding to U.S. application Ser. No. 132,400, to Seiden, who defined medium chain substituents as comprising $C_6$ to $C_{10}$ residues, and Jap. Pat. Pub. No. 2-158,695 to Yoshida, et al., who defined medium chain substituents as comprising $C_4$ to $C_{12}$ residues. The latter publication, however, exemplified only trace amounts of $C_4$ fatty acids, and suggested incorporating 0 to 1 long chain, unsaturated residues as well.) Low calorie triglyceride mixtures having stearic acid at the 1-position and medium and unsaturated residues in the other positions have also been suggested (U.S. Pat. No. 4,832,975 to Yang).

The polymorphism of triglycerides bearing medium and long moieties generally resemble fats bearing long moieties in that they tend to have a stable beta crystal structure. This contributes to graininess of fat mixtures containing them, and, in chocolate compositions, to the appearance of bloom. The preparation of smooth blends require careful substituent selection and/or tempering. It would be desirable to have low calorie fat mixtures free of this disadvantage. It would also be desirable to have a fat which was a true triglyceride but which delivered a minimum of calories and exhibited functionalities which permitted use in a wide variety of products.

DISCLOSURE OF THE INVENTION

An object of the present invention is to provide a new group of low calorie triglycerides and food compositions incorporating them.

It is a principal object of this invention to provide natural low calorie fats.

It is a further object of this invention to provide reduced calorie fats having excellent organoleptic properties and functional characteristics useful in a wide variety of foods.

These and other objects are accomplished by the present invention, which provides mixtures enriched with triglycerides having both long, saturated, preferably $C_{16}$ to $C_{22}$, fatty acid residues and short, preferably $C_2$ to $C_4$, acid residues. These mixtures are employed in edible compositions as low calorie fats. Most preferably, the long fatty acid residues will be $C_{18}$ and the short acid residues will be $C_2$ to $C_3$.

Denoting the aliphatic portion of the long fatty acid substituent as L and the short as S, the mixtures are enriched with one or more SSL, SLS, LLS, and LSL species described by the following formulae:

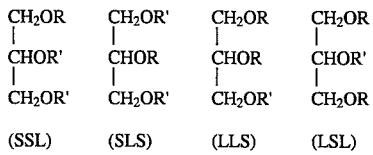

where
each R, independently, is a long chain saturated fatty acid residue having between 16 and 40 carbons, preferably 18 to 22 carbons;
and
each R', independently, is a short chain acid residue having 2 to 5 carbons, preferably 2 to 4 carbons, most preferably 2 to 3 carbons.

Depending upon the preparative procedure (to be more fully described below), the mixtures may also contain triglycerides of the formulae

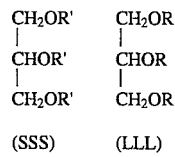

where R and R' are as defined above.

However, preferred mixtures contain essentially no SSS and preferably less than 2%, more preferably less than 1%, LLL.

As depicted above, the triglycerides employed in this invention are compounds consisting of three molecules of the same or different acids esterified to glycerol, 1,2,3-propanetriol, having the formula $(CH_2OH)_2CHOH$. The acids are short $C_2$ to $C_5$ acids, or long and saturated $C_{16}$ to $C_{40}$ acids.

One preferred embodiment is a mixture of at least two of the above described triglycerides, at least one bearing two different short residues as R' groups. Another preferred embodiment is a mixture of at least two triglyceride fats each bearing a similar array of long, saturated residues but a different complement of short chain residues.

Methods of using the low calorie fats and food products incorporating them are also disclosed. The low calorie triglycerides of this invention are especially advantageous in coating fat compositions comprising at least about 75%, preferably at least about 85%, more preferably at least about 90%, by weight SSL and SLS species and between about 0.1 and about 25%, preferably between about 5 and about 10%, by weight LLS and LSL species. In chocolate confections, preferred embodiments are employed in amounts effective to reduce bloom.

The low calorie triglycerides of this invention are also especially advantageous in margarine and shortening fat compositions. Preferred shortening fat embodiments contain at least two triglyceride species bearing long, saturated acid residues and propionic acid, buryrio acid, mixtures of acetic acid and propionic acid, mixtures of acetic acid and buryrio acid, mixtures of propionic acid and buryrio acid or mixtures of acetic acid, propionic acid, and butyric acid residues. Preferred margarine fat embodiments are trans-free and contain 1 to 95%, preferably 5 to 75%, low calorie fats and 5 to 95%, preferably 25 to 95%, edible oil

GENERAL DESCRIPTION OF THE INVENTION

Figure 1:
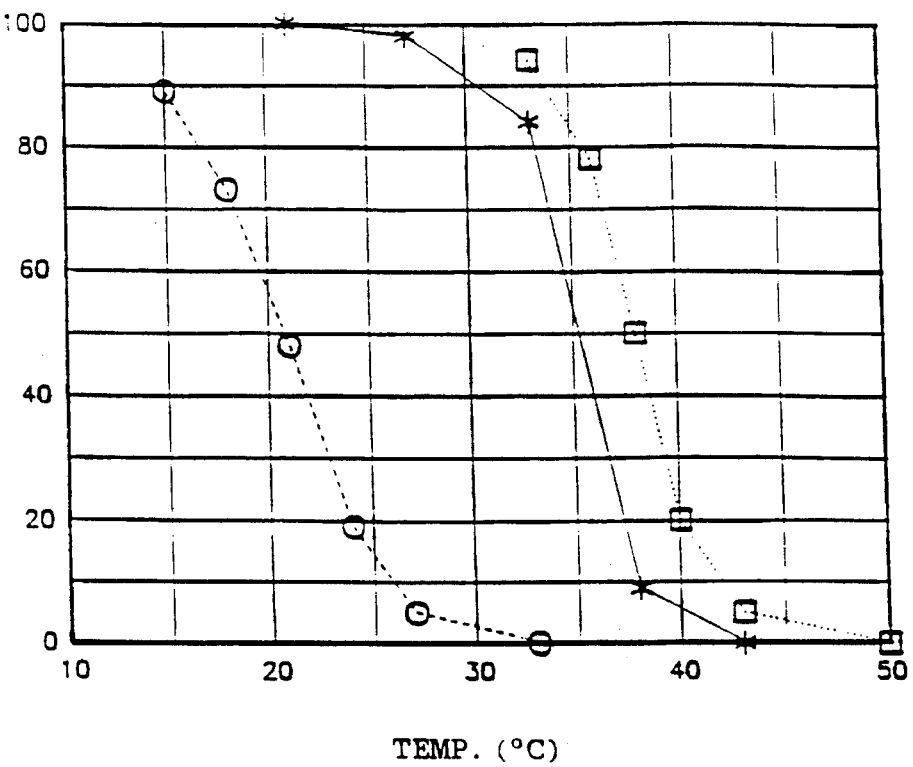
FIG. 1 shows differential scanning calorimetric (DSC) solid fat indices of tempered cocoa butter (- ▷ -), quench cooled cocoa butter (–⊖–), and cocoa butter after several months' storage (····•····) at ambient temperature.

Before descriting the most preferred aspects of the invention, applicants present the following description of the technology, describing in detail the nature of the compositions of the invention, and how to make and use them.

In the practice of this invention, low calorie food products are formulated with mixtures of triglycerides enriched with short ($C_2$ to $C_4$, particularly $C_2$ to $C_3$) acid residues and long ($C_{16}$ to $C_{22}$) fatty acid residues.

The short (volatile) acid residue, R', has no more than 5 carbons, more narrowly 2 to 4, particularly 2 or 3 carbons. R' is derived from a carboxylic acid of the formula SCOOH, where S is a short chain group such as an aliphatic or an hydroxyalkyl having 1 to 4 carbons. As denoted herein, where R' is described as having 2, 3, 4, or 5 carbons, compositions with R' groups having predominantly 2, 3, 4, or 5 carbons are included. Acylation of a glycerol hydroxyl by acid SCOOH results in the attachment of short chain S to the glycercl backbone by means of an ester linkage (—O—(CO)—). Where there is more than one R' attached to a glyceride, the R' groups may be the same or different. As used herein, the term "acid residue" refers to an acyl group comprising a short chain portion, here S, and a carbonyl group, so that R'=S—(CO)—.

Short chain S may be either saturated or unsaturated, straight or branched. Short chain S may be derived from any synthetic or natural organic acid including, but not limited to acetic (ethanoic), propionic (propanoic), burytic (butanoic), valeric (pentanoic), glycolic (hydroxyacetic), lactic (2-hydroxypropanoic), hydracrylic (3-hydroxypropanoic), hydroxybutyric, hydroxypentanoic, and the like acids. As used herein, chemical names include isomeric variations; for example, "butyric acid" includes normal-butyric acid (butanoic) and iso-butyric (2-methylpropanoic) acid, "valeric acid" includes normal-valeric (pentanoic) and iso-valeric (3-methylbutanoic), and so forth. Preferred acids are acetic, propionic, and butyric acids and mixtures of these. Acetic and propionic acids are especially preferred.

Mixtures of acids may also be used, such as, for example, those derived from specific fractions of unhydrogenated, partially hydrogenated or fully hydrogenated dairy butterfat, coconut, palm kernel and the like oils. For example, butter fat has been fractionated, yielding a fraction enriched with triglycerides having 2 residues of at least 16 carbons and 1 residue with 2 to 8 carbons (though the Examples illustrated only 4 to 8 carbons for the shorter moiety, U.S. Pat. No. 4,479,097 to Lansbergen and Kemps, column 5, Tables 2 and 4, and U.S. Pat. No. 4,504,503 to Biernoth and Merk, column 3, Tables 1 and 2); the butterfat stearine fraction was said to improve the butter-like properties of margarine.

The low calorie triglycerides of this invention generally contain 33 to 67 mole % short acid residues. Fatty acid mixtures can contain amounts of medium or long, unsaturated fatty acids to the extent which these can be tolerated without unduly affecting the physical properties of the fat, or the caloric reduction. For example, some products may contain up to 20% medium and/or long, unsaturated triglycerides.

The long fatty acid residue, R, has from 16 to 40 carbons, more narrowly 16 to 24, more narrowly, 18 to 22, and even more narrowly 18 to 20 carbons. In one embodiment, R has predominantly ($\geq 70$ to 80%, or higher) 18 carbons (stearic acid residues). In another embodiment R has $\geq 90\%$ $C_{18}$ (stearic acid residue) R groups. R is an acyl group comprising an aliphatic portion and a carbonyl, and is derived from a fatty acid of the formula LCOOH, where L is a saturated aliphatic group having 15 to 39 carbons; thus, R=L—(CO)—. Acylation of a glycerol hydroxyl by acid LCOOH results in the attachment of long chain L to the glycerol backbone by means of an ester linkage (—O—(CO)—). Where there is more than one R group attached to a glycerol backbone, the R groups may be the same or different.

R may be derived from any synthetic or natural, straight or branched saturated organic acid including, but not limited to, palmitic (hexadecanoic), stearic (octadecanoic), arachidic (eicosanoic), behenic (docosanoic), lignoceric (tetracosaenoic), cerotic (hexacosanoic), montanic (octacosanoic), melissic (triacontanoic), and the like acids. R may also be derived by hydrogenating an unsaturated acid including, but not limited to, palmitoleic (9-hexadecenoic), oleic (cis-9-octadecenoic), elaidic (trans-9-octadecenoic), vaccenic (trans-11-octadecenoic), linoleic (cis,cis-9,12-octadecedienoic), linolenic (9,12,15 -octadecatrienoic and 6,9,12-octadecatrienoic), eleostearic (9,11,13-octadecatrienoic), arachidonic (5,8,11,14-eicosatetraenoic), nervonic (cis-15-tetracosenoic), eicosapentaenoic, docosatetraenoic, docosapentaenoic, docosahexaenoic, and the like acids. Chemical names include isomeric variations.

The various R groups can be mixtures of fatty acids and can be derived, for example, from non-hydrogenated, partially hydrogenated or fully hydrogenated oils such as soybean, safflower, sunflower, high oleic sunflower, sesame, peanut, corn, olive, rice bran, babassu nut, palm, mustard seed, cottonseed, poppyseed, low erucic rapeseed, high erucic rapeseed, shea, marine, meadowfoam and the like oils. Preferred oils are hydrogenated, preferably fully hydrogenated. Hydrogenated fats having at least about 70%, preferably at least about 75%, stearic acid residues such as hydrogenaced peanut oil, hydrogenated olive oil, hydrogenated soybean oil, hydrogenated sesame oil, and hydrogenated corn oil are especially desirable for some embodiments. Other embodiments employ hydrogenated fats having at least about 90% stearic acid residues, such as hydrogenated sunflower oil, hydrogenated safflower oil and hydrogenated canola. Fatty acids derived from processed or unprocessed tallow, lard, shea butter, and dairy butter, or plant waxes such as jojoba may also be used. Specific fractions of processed or unprocessed oils, fats, or waxes may be used, and are especially advantageous in some embodiments.

The oils, fats, or waxes may be hydrogenated before or after incorporation into the low calorie triglycerides of this invention. The mixtures can contain amounts of medium or unsaturated long fatty acids to the extent which these can be tolerated without unduly affecting the physical properties of the fat, or the caloric reduction. For example, some products may contain up to 20% medium and/or unsaturated long fatty acids. The caloric reduction is best taken advantage of when the level of these acids is maintained at less than 15%, more desirably less than 10%.

Some of the compounds of this invention may be described by the formula

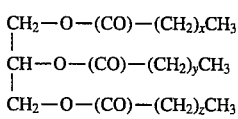

where x, y, and z=n or m n=0, 1, 2, or 3, m=16, 18, 20 or 22, and

14≦(x+y+z)≦47.

The long and short substituents are selected to provide a discernible fatty character in the mixtures. An advantage of the present invention is that functional properties can be modulated by the selection of S and L groups as well as by the proportions of SSS, SLS, SSL, LLS, LSL and LLL components in the mixtures. Formulations for chocolate or confectionery applications, for example, can employ groups or components yielding high, sharply melting mixtures, salad oils can employ groups or components yielding medium melting mixtures that do not readily crystallize upon refrigeration, margarines and shortenings can employ groups or components yielding plastic mixtures, bakery products may employ groups or components stable to oxidation on storage, and so forth. Particular formulations are set forth hereinafter.

The molar ratio of S to L groups in the SSS, SLS, SSL, LLS, LSL and LLL low calorie mixtures of this invention may be determined using proton or carbon nuclear magnetic resonance (hereinafter referred to as NMR), or any quantitative procedure known to those skilled in the art. The S/L ratio generally varies between 0.5 and 2.0. Using this parameter, many of the mixtures of this invention fall into one of three major groups: the first has an S/L ratio of 0.5 to 1.0; the second, 1.0 to 1.5; and the third, 1.5 to 2.0.

In some embodiments, mixtures having higher capillary melting points, e.g., melting above 50° C., preferred for certain food applications, fall into the first group and have S/L ratios that vary between 0.5 and 1.0. Some mixtures having mid-range melting points, e.g., melting between ~25° to 30° and 50° C., preferred for other applications, fall into the second group and have S/L ratios that vary between 1.0 and 1.5. Some mixtures having lower melting points, e.g., melting below 25° C., fall into the third group and have S/L ratios that vary between 1.5 and 2.0. Specific examples are set forth hereinafter.

In one embodiment, the triglyceride mixtures of this invention have capillary melting points from 10° to 25° C. Another melts at 20° to 30° C. Another embodiment melts at 33° to 39° C. Others melt above 40° C., with one embodiment having a capillary melting point of 50° to 60° C. An advantage of the present invention is that the melting point ranges can be tailored by the choice of the short and long acid residues and the amount of SSL/SLS and SLL/LSL in the mixtures. Mixtures can be further varied by adding SSS or LLL species, or conventional triglycerides.

Moreover, the choice of the short and long acid residues and the amount of SSL/SLS, SLL/LSL, SSS, LLL and conventional fats in the mixtures can be used to modulate the solids contents for fats having the same (or different) capillary melting points so that the functional properties may be further modified. By the term "solids content" is meant the percentage of a fat that exists in crystalline form at a given temperature. Solid fat contents (herein abbreviated S.F.C.) are determined using nuclear magnetic resonance according to A.O.C.S. Method Cd 16-81. Unless otherwise indicated, solid fat indices (herein abbreviated S.F.I.) are determined using dilatometry according to A.O.C.S. Method Cd 10-57. Solids percentages are reported at 50° F. (10° C.), 70° F. (21.1° C.), 80° F. (26.7° C.), 92° F. (33.3° C.), and 100° F. (37.8° C.). Example S/L ratios, melting points, S.F.C.'s, and S.F.I.'s are given hereinafter.

The molar percentage of LLS and LSL in the mixtures can range from 0 to nearly 100%. In some embodiments, the LLS and LSL molar percentage is less than about 25%, preferably less than 15%, and even more preferably less than 5%. In others, the molar percentage is higher, ranging between 25 and 40%. One preferred embodiment is 15 to nearly 20 mole percent LLS/LSL; another is 20 to nearly 25%; another is 25 to 30%.

The molar percentage of SLS and LSS in the mixtures can range between 0 to nearly 100%, more narrowly 10 and 90%, even more narrowly 15 to 85%. In some embodiments, the LSS/SLS molar percentage ranges between 75 and 100%; in others, between 85 and 100%. One preferred embodiment is 40 to nearly 60 mole percent LSS/SLS; another is 60 to nearly 70%; another is 90 to 100%. One especially preferred embodiment has greater than 80%, preferably greater than 85%, even more preferably greater than 97% SSL and SLS. It is advantage of the invention that low calorie fats containing large amounts of LSS/SLS have small amounts of L moieties.

The molar percentage of LLL in the mixtures is generally under 10%, more narrowly less than 5%. In some embodiments, mixtures having less than 3% LLL are preferred. In others, less than 1% is preferred. The molar percentage of SSS in the mixtures is generally under 10%; preferred mixtures contain less than 5% SSS, more narrowly less than 3%; many embodiments contain essentially no SSS species.

Based on relative proportions of S and L substituents, the low calorie triglyceride mixtures of this invention can be placed into three major groups:

Group I comprises mixtures wherein the molar ratio of short to long (S/L) substituents falls between 0.5 and 1.0. These mixtures tend to have higher capillary melting points; many embodiments melt above 50° C., and thus are solids at room temperature.

Group II comprises mixtures wherein the molar ratio of short to long (S/L) substituents varies between 1.0 and 1.5. These mixtures tend to have mid-range melting points; many embodiments melt between ~25° and ~50° C.

Group III comprises mixtures wherein the short to long (S/L) molar ratio varies between 1.5 and 2.0. These mixtures tend to have lower melting points. Some embodiments melt below 25° C., and are fluids at room temperature.

One embodiment of this invention comprises a triglyceride mixture of:

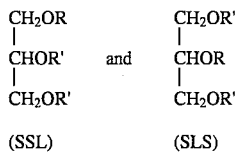

Preferred mixtures of this type contain a mixture of at least two R' groups and more SSL than SLS. Many of the compounds of this type may be described by the formula

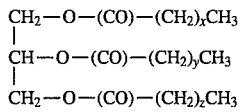

where x, y, and z=n or m n=0, 1, 2, or 3 m=16, 18, 20 or 22, and $14 \leq (x+y+z) \leq 28$.

One especially preferred embodiment has $x+y+z=17$.

Another embodiment of this invention comprises a triglyceride mixture of:

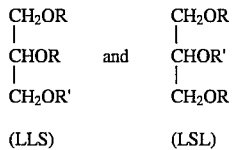

These generally have higher melting points than mixtures of SSL and SLS, especially where the LSL species predominates. Some preferred mixtures contain a mixture of two or more R groups, such as for example, R groups derived from cottonseed, soybean or fish oils; some of these contain a mixture of two or more R' groups, such as, for example a mixture of R' groups derived from acetic and propionic acid.

Many of the LLS/LSL mixtures can be described by the formula

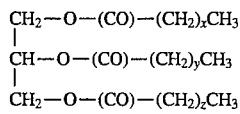

where x, y, and z=n or m n=0, 1, 2, or 3, m=16, 18, 20 or 22, and $29 \leq (x+y+z) \leq 46$.

Component triglycerides making up the low calorie fat mixtures of this invention may be prepared using synthetic procedures known to those skilled in the art, such as, for example, directly esterifying glycerol or glycerol esters with fatty acids, fatty acid halides (notably chlorides) or fatty acid anhydrides, transesterifying glycerol with fatty acid esters, or interesterifying long and short chain triglycerides for such time and under such conditions that triglycerides bearing long and short residues form. Starting materials for triglyceride preparations may be obtained commercially or isolated from natural sources. Alternatively, component triglycerides may be isolated from natural or processed fats or oils, or fractions thereof, as discussed above. Examples prepared are set out in the next section.

Some desirable triglyceride mixtures are prepared using a random interesterification of triacetin, tripropionin and/or tributyrin with a substantially hydrogenated fat having at least about 70%, in some cases at least about 75%, more preferably at least about 90%, stearic acid residues. An advantage of this invention is that the preparative procedure for many mixtures can be facilitated by employing at least two triglycerides bearing only short triglycerides. For example, because of solubility differences, triacetin reacts sluggishly with hydrogenated canola, but in the presence of tripropionin, the reaction is facilitated.

Some preparative procedures for triglycerides bearing short and long substituents have been published. Interesterification of a shortening basestock with triacetin yielded an improved plastic product (though all the Examples employed partially, not fully, hydrogenated basestocks; see U.S. Pat. No. 2,614,937 to Baur and Lange). Acetylated monoglycerides have been discussed above. An acetylated monoglyceride prepared from lard, cottonseed oil or partially hydrogenated vegetable oil has been disclosed as useful in lowering cholesterol (U.S. Pat. No. 4,272,548 to Gatzen, et al.). Triglycerides bearing palmitic and butyric residues were synthesized for study as pancreatic lipase and human milk bile lipase substrates (in Clement, G., et al., *Biochem. Biophys. Res. Commun.* 8: 238–242 (1962) and Wang, C. S., et al., cited previously, respectively).

The low calorie triglycerides of this invention may be incorporated either alone, or in combination with another fat and/or fat mimetic, into any food composition, or used in conjunction with any edible material. Other fats include natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like. Other fat mimetics include any heretofore suggested as edible fat replacements, including, but not limited to, sugar esters, neoalkyl esters, polyglycerol esters, malonate esters, propoxylated glycerols, retrofats, carboxy/carboxylates, polyvinyl alcohol esters and the like. When employed either alone or in products with other fats, they are desirably added in amounts effective to provide a significant caloric reduction of the calories due to fat. For example, a 10% or greater replacement would be effective for this purpose, and replacements of at least 25%, more particularly 50 to 100%, are desired in many cases.

The term "edible material" is broad and includes anything edible, whether or not intended for nutrition, e.g., it can be an additive such as an antioxidant for fats or oils, an antispatter agent, an emulsifier, a texture modifier such as a plasticizer for chewing gum, a component for cosmetics, or other minor functional ingredient such as a carrier or diluent for use in flavorings, pharmaceuticals, and the like.

Broadly speaking, the reduced calorie triglycerides of this invention can be employed as fat replacements in fat-containing edible emulsions comprising an oil phase and an aqueous phase, including those high in fat, such as margarines and salad dressings, and those high in water, such as low fat spreads. The triglycerides of this invention can be employed as full or partial fat substitutes in dairy, meat, nut, egg, and other food products having a high natural fat component, and in vegetable, cereal and other products having a low natural eat component. The triglycerides of this invention can be employed as ingredients for all types of leavened baked products, both yeast raised and chemically leavened, and unleavened baked products, and as coatings or coating ingredients for the same types of products. The triglycerides of this invention can be employed as an ingredient or a coating for snack food products, as well as a frying oil or a frying oil ingredient for fried snacks. In addition, the low calorie triglycerides of the present invention can be employed to form edible barrier layers, either on the exposed surfaces of foods or as internal barrier layers used to separate various portions of a food product, e.g., in frozen pizza, nut coatings, or as a barrier between a dessert filling and an outer edible shell in fruit filled cookies and the like.

Representative of fat-containing food products which can contain, in addition to other food ingredients, the low calorie triglycerides of this invention in full or partial replacement of natural or synthetic fat are: frozen desserts, e.g., frozen novelties, ice cream, sherbet, ices, and milk shakes; salad dressings; mayonnaises and mustards; dairy and non-dairy cheese spreads; margarine, margarine substitutes and blends; flavored dips; flavored bread or biscuit spreads; filled dairy products such as filled cream and filled milk; frying fats and oils; cocoa butter replacements and blends; candy, especially fatty candies such as those containing peanut butter or chocolate (to which antibloom properties may be imparted); reformed and comminuted meats; meat substitutes and extenders; egg products and substitutes; nut products such as peanut butter; vegetable and fruit products; pet foods; whipped toppings; compound coatings; coffee lighteners, liquid and dried; puddings and pie fillings; frostings and fillings; chewing gum; breakfast cereals; bakery products, e.g., cakes, breads, rolls, pastries, cookies, biscuits, and savory crackers and mixes or ingredient premixes for any of these. The low calorie triglycerides of this invention may also be employed in any flavor, nutrient, drug or functional additive delivery system.

An advantage of the present invention is that the low calorie triglycerides of this invention may be mixed with natural oils so that the ratio of unsaturated to saturated residues in certain food products such as margarine is greater than 2.5. In one embodiment, the polyunsaturated to saturated ratio lies between 1 and 2; in another, the ratio is greater than 2.

The following is a list of representative, but not limiting, triglycerides which may be employed in the mixtures of this invention:

(1) 2-Butyryl-1,3-distearoyl Glyceride $CH_2-O-(CO)-(CH_2)_{16}CH_3$
$CH-O-(CO)-(CH_2)_2CH_3$
$CH_2-O-(CO)-(CH_2)_{16}CH_3$ (2) 1,2-Dibutyryl-3-stearoyl Glyceride $CH_2-O-(CO)-(CH_2)_2CH_3$
$CH-O-(CO)-(CH_2)_2CH_3$
$CH_2-O-(CO)-(CH_2)_{16}CH_3$ (3) 1-Butyryl-2,3-distearoyl Glyceride $CH_2-O-(CO)-(CH_2)_2CH_3$
$CH-O-(CO)-(CH_2)_{16}CH_3$
$CH_2-O-(CO)-(CH_2)_{16}CH_3$ (4) 1,3-Dibutyryl-2-stearoyl Glyceride $CH_2-O-(CO)-(CH_2)_2CH_3$
$CH-O-(CO)-(CH_2)_{16}CH_3$
$CH_2-O-(CO)-(CH_2)_2CH_3$ (5) 2-Isobutyryl-1,3-distearoyl Glyceride $CH_2-O-(CO)-(CH_2)_{16}CH_3$
$CH-O-(CO)-CH(CH_3)_2$
$CH_2-O-(CO)-(CH_2)_{16}CH_3$ (6) Tristearoyl Glyceride $CH_2-O-(CO)-(CH_2)_{16}CH_3$
$CH-O-(CO)-(CH_2)_{16}CH_3$
$CH_2-O-(CO)-(CH_2)_{16}CH_3$ (7) Tributyryl Glyceride $CH_2-O-(CO)-(CH_2)_2CH_3$
$CH-O-(CO)-(CH_2)_2CH_3$
$CH_2-O-(CO)-(CH_2)_2CH_3$ (8) 1-Arachidoyl-2,3-dipropionyl Glyceride $CH_2-O-(CO)-(CH_2)_{18}CH_3$
$CH-O-(CO)-CH_2CH_3$
$CH_2-O-(CO)-CH_2CH_3$ (9) 1,2-Dipalmitoyl-3-valeryl Glyceride $CH_2-O-(CO)-(CH_2)_4CH_3$
$CH-O-(CO)-(CH_2)_{14}CH_3$
$CH_2-O-(CO)-(CH_2)_{14}CH_3$

(10) 2-Propionyl-1,3-distearoyl Glyceride $CH_2-O-(CO)-(CH_2)_{16}CH_3$
$CH-O-(CO)-CH_2CH_3$
$CH_2-O-(CO)-(CH_2)_{16}CH_3$

(11) 1-Acetyl-2-propionyl-3-stearoyl Glyceride $CH_2-O-(CO)-CH_3$
$CH-O-(CO)-CH_2CH_3$
$CH_2-O-(CO)-(CH_2)_{16}CH_3$

(12) 1-Butyryl-2-palmitoyl-3-stearoyl Glyceride $CH_2-O-(CO)-(CH_2)_2CH_3$
$CH-O-(CO)-(CH_2)_{14}CH_3$
$CH_2-O-(CO)-(CH_2)_{16}CH_3$

(13) 1-Behenoyl-2-butyryl-3-stearoyl Glyceride $CH_2-O-(CO)-(CH_2)_{20}CH_3$
$CH-O-(CO)-(CH_2)_2CH_3$
$CH_2-O-(CO)-(CH_2)_{16}CH_3$ -continued

(14) 1-Palmitoyl-2-propionyl-3-stearoyl Glyceride $$\text{CH}_2-\text{O}-(\text{CO})-(\text{CH}_2)_{14}\text{CH}_3$$
$$\text{CH}-\text{O}-(\text{CO})-\text{CH}_2\text{CH}_3$$
$$\text{CH}_2-\text{O}-(\text{CO})-(\text{CH}_2)_{16}\text{CH}_3$$

(15) 1-Palmitoyl-2,3-distearoyl Glyceride $$\text{CH}_2-\text{O}-(\text{CO})-(\text{CH}_2)_{14}\text{CH}_3$$
$$\text{CH}-\text{O}-(\text{CO})-(\text{CH}_2)_{16}\text{CH}_3$$
$$\text{CH}_2-\text{O}-(\text{CO})-(\text{CH}_2)_{16}\text{CH}_3$$

(16) 1,2-dipalmitoyl/stearoyl-3-valeryl Glyceride $$\text{CH}_2-\text{O}-(\text{CO})-(\text{CH}_2)_3\text{CH}_3$$
$$\text{CH}-\text{O}-(\text{CO})-\text{L}$$
$$\text{CH}_2-\text{O}-(\text{CO})-\text{L}$$

where the L's comprise a mixture of 90–97%
$-(\text{CH}_2)_{16}\text{CH}_3$ and 3–10% $-(\text{CH}_2)_{14}\text{CH}_3$

(17) 2-Acetyl/propionyl-1,3-distearoyl Glyceride $$\text{CH}_2-\text{O}-(\text{CO})-(\text{CH}_2)_{16}\text{CH}_3$$
$$\text{CH}-\text{O}-(\text{CO})-\text{S}$$
$$\text{CH}_2-\text{O}-(\text{CO})-(\text{CH}_2)_{16}\text{CH}_3$$

where S comprises a 1:1 mixture of $-\text{CH}_3$ and $-\text{CH}_2\text{CH}_3$

(18) 2-Lactoyl-1,3-distearoyl Glyceride $$\text{CH}_2-\text{O}-(\text{CO})-(\text{CH}_2)_{16}\text{CH}_3$$
$$\text{CH}-\text{O}-(\text{CO})-\text{CH(OH)}\text{CH}_3$$
$$\text{CH}_2-\text{O}-(\text{CO})-(\text{CH}_2)_{16}\text{CH}_3$$

(19) 2-Butyryl-1,3-di(10-methyl)stearoyl Glyceride $$\text{CH}_2-\text{O}-(\text{CO})-(\text{CH}_2)_8\text{CH}(\text{CH}_3)(\text{CH}_2)_7\text{CH}_3$$
$$\text{CH}-\text{O}-(\text{CO})-(\text{CH}_2)_2\text{CH}_3$$
$$\text{CH}_2-\text{O}-(\text{CO})-(\text{CH}_2)_8\text{CH}(\text{CH}_3)(\text{CH}_2)_7\text{CH}_3$$

(20) 1-Isobutyryl-3-(10-methyl)stearoyl-2-stearoyl Glyceride $$\text{CH}_2-\text{O}-(\text{CO})-\text{CH}(\text{CH}_3)_2$$
$$\text{CH}-\text{O}-(\text{CO})-(\text{CH}_2)_{16}\text{CH}_3$$
$$\text{CH}_2-\text{O}-(\text{CO})-(\text{CH}_2)_8\text{CH}(\text{CH}_3)(\text{CH}_2)_7\text{CH}_3$$

Other example structures and compounds are set out in the next section, with further particulars as to syntheses and/or physical properties. Also illustrated in the next ection are mixtures derived from natural oils. other nonlimiting examples of component trigiycerides so derived include compounds of the formula:

Acetylated Hydrogenated Soybean Oil Derivatives $$\begin{array}{lll}
\text{CH}_2\text{OR} & \text{CH}_2\text{OR} & \text{CH}_2\text{OR} \\
\text{CHO(CO)CH}_3 & \text{CHOR} & \text{CHO(CO)CH}_3 \\
\text{CH}_2\text{O(CO)CH}_3 & \text{CH}_2\text{O(CO)CH}_3 & \text{CH}_2\text{OR}
\end{array}$$

$$\begin{array}{ll}
\text{CH}_2\text{O(CO)CH}_3 & \text{CH}_2\text{OR} \\
\text{CHOR} & \text{CHOR} \\
\text{CH}_2\text{O(CO)CH}_3 & \text{CH}_2\text{OR}
\end{array}$$

where the R groups are derived from hydrogenated soybean oil

Low Calorie Hydrogenated High Oleic Sunflower Oil Derivatives $$\begin{array}{lllll}
\text{CH}_2\text{OR} & \text{CH}_2\text{OR'} & \text{CH}_2\text{OR} & \text{CH}_2\text{OR} & \text{CH}_2\text{OR} \\
\text{CHOR'} & \text{CHOR} & \text{CHOR} & \text{CHOR'} & \text{CHOR} \\
\text{CH}_2\text{OR'} & \text{CH}_2\text{OR'} & \text{CH}_2\text{OR'} & \text{CH}_2\text{OR} & \text{CH}_2\text{OR}
\end{array}$$

where R' is a mixture of $-(\text{CO})-\text{CH}_3$ and $-(\text{CO})-(\text{CH}_2)_2\text{CH}_3$ and the R groups are derived from hydrogenated high oleic sunflower oil.

Acetylated/Propionylated Hydrogenated Shea Oil Derivatives $$\begin{array}{lllll}
\text{CH}_2\text{OR} & \text{CH}_2\text{OR'} & \text{CH}_2\text{OR} & \text{CH}_2\text{OR} & \text{CH}_2\text{OR} \\
\text{CHOR'} & \text{CHOR} & \text{CHOR} & \text{CHOR'} & \text{CHOR} \\
\text{CH}_2\text{OR'} & \text{CH}_2\text{OR'} & \text{CH}_2\text{OR'} & \text{CH}_2\text{OR} & \text{CH}_2\text{OR}
\end{array}$$

where R' is a mixture of $-(\text{CO})-\text{CH}_3$ and $-(\text{CO})-\text{CH}_2\text{CH}_3$, and the R groups are derived from hydrogenated shea oil and the like.

DESCRIPTION OF PREFERRED EMBODIMENTS

This invention is based upon surprising findings that short chain acids other than acetic or in addition to acetic can be employed to improve the functional properties of acetostearins. In some cases, the properties can be drastically changed simply by mixing the acetyl residues with one or more other volatile acid residues, by substituting one or more volatile acid residues for acetyl residues, or by admixing acetostearins with one or more structurally similar fats that have different short substituents, even though the similar fat, by itself, more closely resembles pure acetostearins than it does the mixture.

Moreover, certain combinations of triglycerides bearing short and saturated, long triglycerides, especially mixtures that contain an enriched amount of at least two short chain acids, are low in calories and have an array of desirable characteristics in food applications, including oxidative stability, smooth organoleptic properties, unique solids profiles, and resistance to bloom. Food products employing these desirable triglycerides aldo exhibit moisture retention and interestering baking characteristics.

In one preferred embodiment, the low calorie triglycerides of this invention bear mixtures of at least two short chain acid residues. Preferred mixtures are acetic and propionic acid residues, acetic and butyric acid residues, propionic and butyric acid residues, and acetic, propionic, and butyric acid residues.

In another preferred embodiment, the low calorie triglycerides are mixtures of at least two triglycerides bearing long, saturated residues but different complements of short chain groups. Thus, mixtures of at least two triglycerides bearing acetic acid residues or propionic acid residues or butyric acid residues or a mixture of acetic acid and propionic acid residues, or a mixture of acetic acid and butyric acid residues, or a mixture of propionic acid residues and butyric acid residues, or a mixture of acetic acid, propionic acid, and burytic acid residues with long, saturated residues are encompassed. Preferred combinations of this type are mixtures containing at least two triglycerides, each bearing acetic, propionic or butyric acid residues and long, saturated residues.

Candy coating Fats

The low calorie triglycerides of this invention are especially advantageous in coating compositions, especially coatings for candies and bakery and dessert products. A preferred embodiment comprises a mixture of at least two triglycerides of the formulae

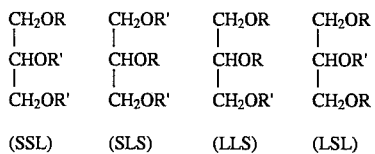

(SSL)    (SLS)    (LLS)    (LSL)

wherein
each R, independently, is a long chain saturated fatty acid residue having between 18 and 22 carbons,
each R', independently, is a short chain acid residue having 2 to 4 carbons derived from acetic acid, propionic acid, and/or butyric acid,
comprising at least about 75%, preferably at least about 85%, more preferably at least about 90%, by weight SSL and SLS species and between about 0.1 and about 25%, preferably between about 2 and about 10%, by weight LLS and LSL species.

One especially preferred embodiment has R' groups comprising a mixture of acetic and propionic acid residues.
The composition contains about 10 to about 25, preferably about 15 to about 25, particularly about 23, weight percent acetic acid residues and about 0.1 to about 10, preferably about 0.5 to about 5, particularly about 4, weight percent propionic acid residues. As has been described above, these desirable coatings can be prepared by blending diacetin and dipropionin saturated fats or by interesterifying triacetin, tripropionin, and a fat enriched with long saturated residues such as hydrogenated canola, hydrogenated soybean oil or tristearin.

For example, an especially desirable coating fat is prepared by randomly interesterifying, using a reactant molar ratio of 11:1:1, triacetin, tripropionin and hydrogenated canola and then steam deodorizing. Chocolate coatings formulated using the triglyceride mixture so obtained have a melting profile striking similar to coatings containing cocoa butter (see, for example, FIG. 4), but are low in calories and bloom resistant (an advantage more fully discussed hereinafter).

Other desirable coating fats contain, as short chain substituents, a mixture of acetic acid and butyric acid residues, a mixture of propionic and butyric acid residues, or a mixture of acetic, propionic, and butyric acid residues. A typical coating fat has a melting point of about 32° to about 38° C., a solids content of at least about 50% at about 10° C., and a solids content of less than about 5% at about 30° C.

An advantage of this invention is that preferred chocolate-like coating fat compositions can be employed in amounts effective to reduce bloom, i.e., in amounts that reduce visually apparent bloom at least about 35%, preferably at least about 50%. As is familiar to the skilled artisan, "bloom" is a separation of fat crystals from the matrix of a chocolate coating, generally caused by separation of cocoa butter from the matrix and extrusion or recrystaliization of fat to or on the surface with consequent white layer or splotches. Bloom is usually ascribed to partial liquefication (due, for instance, to temperature fluctuations) and then recrystallization of the fat which sometimes migrates to the surface. Although tempering, the formation of stable crystals via a commonly used cooling and slow heating process, can help in retarding bloom, bloom remains a recurring problem in the chocolate confection industry. Preferred coating fat embodiments of this invention reduce visually apparent bloom by at least about 90% over two or three temperature (warming and cooling) cycles and have a unique crystal structure that requires no tempering. In fact, some can be quench cooled.

Surprisingly, it has been found that a number of the low calorie fats of this invention, when employed in chocolate-type confectionery products, inhibit the formation of visually apparent bloom. For example, when the acetyl/propionyl stearin mixtures disclosed above are used as the fat substitute in chocolate-like confectionery compositions, the incidence of visually apparent bloom is greatly delayed. It is a further advantage of the present invention that the tempering step in the manufacture of the confections can be eliminated when the preferred fats are employed. Moreover, especially preferred confection embodiments can withstand fluctuations in temperature that usually give rise to bloom in chocolate confections even when the chocolate blend has been quench cooled during manufacture. The onset of visually apparent bloom can be delayed for at least about a month, preferably for at least about 6 months, or prevented.

Another advantage of the present invention is that preferred coating fats are compatible with cocoa butter in all proportions. Thus, confections employing the low calorie triglycerides in partial replacement of cocoa butter is greatly facilitated. For example, coating fats of this invention can replace at least about 60% or more of the natural confectionery fat ingredient such as cocoa butter, which can make up at least about 35% of the chocolate. A typical chocolate confectionery composition, for example, contains about 5% to about 40% by weight chocolate flavoring (including chocolate liquor or cocoa which contain some inherent fat), about 25% to about 40% by weight fat ingredients, and about 0.001% to 40% by weight sweetener.

One preferred coating fat of the invention comprises at least 95% triglycerides bearing one long chain fatty acid residue derived from a fat containing at least 90% 18 carbon or higher fatty acid residues hydrogenated to an I.V. value of 3 or less and two short chain residues, each selected from the group consisting of acetic and propionic acid residues in a molar ratio of 51 to 13, said fat being essentially trans-free using A.O.C.S. Method Cd 14-61 and beta crystal free and having the following physical properties:

a Mettler Drop point of about 95° F. using A.O.C.S. Method Cc 18-80;

a smoke point of about 260° F. using A.O.C.S. Diethod Cc 9a-48;

a flash point of about 470° F. using A.O.C.S. Method 9a-48;

a fire point of about 495° F. using A.O.C.S. Method 91-48;

a congeal point of about 33.8° C. using A.O.C.S. Method Ca 14-59;

a specific gravity at 60° C. of about 0.9337 using A.O.C.S. Method Cc 10b-25;

a peroxide value of about 0.45 meq/kg using A.O.C.S. Method 8-53;

a refractive index at 60° C. of about 1.4385 using A.O.C.S. Method Cc 7-25;

a saponification value of about 347 using A.O.C.S. Method 3-25;

an oxidation stability using A.O.C.S. Method Cd 12-57 for at least 290 hours;

a free fatty acid value of about 0.78% using A.O.C.S. Method 5a-40;

an S.F.C. of about 82.1% at 50° F., about 78.4% at 70° F., about 71.7% at 80° F., about 29.9% at 92° F., and about 4.9% at 100° F. using A.O.C.S. Method Cd 16-81;

a viscosity of about 35.1 cps at 100° F. and about 19.7 cps at 150° F.;

a heat of fusion of about 99.4 mJ/mg;

A Lovibond Color of about 20 Red/77 Yellow using a 1 inch column following A.O.C.S. Method Cc 13b-45;

resistance to bloom visually apparent to an analyst trained in identifying and evaluating bloom; and essentially no crystals exceeding 8 u observed on microscopic examination under polarized light.

Margarine Fats

The low calorie triglycerides of this invention are also especially advantageous in margarine fat compositions. Preferred margarine fat embodiments contain at least two triglyceride species bearing long, saturated acid residues and propionic acid, butyric acid, mixtures of acetic acid and propionic acid, mixtures of acetic acid and butyric acid, mixtures of propionic acid and butyric acid or mixtures of acetic acid, propionic acid, and butyric acid residues. Triglyceride mixtures having at least two different long chain moieties are especially preferred for some embodiments, such as, for example, long chain residues obtained from hydrogenated cottonseed or hydrogenated fish oils.

Advantageously, the margarine fats which are either mixtures of individual esters, each containing a distinct short acid species, or mixed esters where at least some of the triglycerides contain two difference short acid residues in addition to a long acid, have lower saponification values than corresponding acetylated triglycerides of similar melting point. It is a practical advantage that lower melting points and broader melting ranges can be achieved, preferably with decreased graininess, than for acetylated triglycerides. The techniques employed in the art, namely employing some degree of unsaturation, shorter long chain fatty acids (e.g., 14 to 16 carbons), medium chain fatty acids (e.g., 8 to 12 carbons), or higher levels of acetic acid, can still be employed is desired; however, these techniques can be dispensed with by the invention. A further and related advantage appears from the ability, as compared to acetylated triglycerides, to obtain a fully saturated oil blend having less $C_{16}$ and $C_{14}$ fatty acids. Thus, trans oleic acid-free margarines can be obtained which also have decreased levels of palmitic and lauric acids. This permits a higher relative proportion of stearic or higher acid and thus enhances the ability to produce a low-calorie product.

The fat mixtures are prepared to yield desirable S.F.I. values. For example, SFI values required for an oil phase to be used in a stick margarine are a minimum solids content of about 15% at 50° F., a minimum solids content of about 7% at 70° F.; and a maximum solids content of about 5% at 92° F. Preferably, the maximum solids content at 92° F. will be less than 4%, most preferably between 1½ to 3 ½ % at 92° F. At this specification, the margarine may be formed and wrapped satisfactorily, maintaining the stick form without substantial oil separation at room temperature and yet remains rapid melting on the tongue at about 98° F. A more preferred SFI profile will show solid contents within the following ranges:

| Temperatures | Solids (%) |
| --- | --- |
| 50° F. | 16 to 31 |
| 70° F. | 11 to 18 |
| 92° F. | 3.5 maximum |

Desirably, the stick margarine should remain firm at ordinary room temperature up to about 80° F., and will therefore most preferably have an SFI value at this temperature within the range of from about 6 to about 10.

The SFI solids values required for an oil phase to be used in formulating a tub margarine are a minimum solids content of about 8% at 50° F., and a minimum solids content of about 3% at 70° F. and a maximum solids content of about 9% at 92° F. Preferably, the SFI profile shows solids contents in the following ranges:

| Temperatures | Solids (%) |
| --- | --- |
| 50° F. | 9 to 15 |
| 70° F. | 5 to 10 |
| 92° F. | 3.5 maximum |

One embodiment employs a ratio of low calorie triglycerides to edible oil between 20:80 and 30:70. An example composition comprises corn oil and one or more low calorie triglycerides selected from the group consisting of dibutyryl stearin and butyryl distearin. Other examples are set forth herinafter.

In the practice of formulating margarines according to this embodiment, effective amounts of low calorie triglycerides are mixed with edible oils to yield structured lipid compositions. By the farm "edible oil" is meant any natural or synthetic lipid, or mixtures of such lipids, which flow at 20° C. and are suitable for use in human foods. Preferred edible oils are liquid at 20° C., with many embodiments liquid at 25° C. Preferred margarine fat compositions contain 1 to 95%, preferably 5 to 75%, low calorie fats and 5 to 95%, preferably 25 to 95%, edible oil.

Edible oils, which are predominantly liquid at 20° C., include semi-liquid oils that contain significant solid fat which can increase their viscosities. Edible oils include vegetable oils such as soybean, safflower, sunflower, high oleic sunflower, sesame, peanut, corn, olive, rice bran, canola, palm, cottonseed, rapeseed, high erucic rapeseed, carrot, evening primrose, borage, and meadowfoam oils. Edible oils also include animal oils such as marine oils, lard, tallow, and dairy butter. Specific fractions of edible oils may be employed. Mixtures of oils and/or fractions may be used.

An advantage of the invention is that the margarines prepared using the low calorie triglycerides of this invention can be formulated so the resulting compositions are trans-free. Most natural fats and oils contain only cis double bonds, but partial hydrogenation results in the formation of trans fatty acids, which have been recently shown to raise low density lipoprotein serum cholesterol levels and to lower high density lipoprotein serum cholesterol levels in adults fed fats having these acids (Mensink, R. P., and Katan, M. B., *New Eng. Jour. Med.*, 323: 439–445 (1990)). Since this invention employs natural oils and fully hydrogenated oils, these isomers can be eliminated from the food products.

One preferred margarine fat of the invention comprises an edible oil and at least 95% triglycerides bearing a mixture of long chain fatty acid residues derived from a fat containing at least 90% 18 carbon or higher fatty acid residues hydrogenated to an I.V. value of 3 or less and butyric acid in a molar ratio of about 46 to 54, said triglycerides being essentially trans-free using A.O.C.S. Method Cd 14-61 and beta crystal free and having the following physical properties:

- a Mettler Drop point of about 87.6° F. using A.O.C.S. Method Cc 18-80;
- a smoke point of about 310° F. using A.O.C.S. Method Cc 9a-48;
- a flash point of about 480° F. using A.O.C.S. Method 9a-48;
- a fire point of about 510° F. using A.O.C.S. Method 91-48;
- a congeal point of about 30.6° C. using A.O.C.S. Method Ca 14-59;
- a specific gravity at 60° C. of about 0.9097 using A.O.C.S. Method Cc 10b-25;
- a peroxide value of about 0.20 meq/kg using A.O.C.S. Method 8-53;
- a refractive index at 60° C. of about 1.4396 using A.O.C.S. Method Cc 7-25;
- a saponification value of about 287 using A.O.C.S. Method 3-25;
- an oxidation stability using A.O.C.S. Method Cd 12-57 for at least 295 hours;
- a free fatty acid value of about 0.23% using A.O.C.S. Method 5a-40;
- an S.F.C. of about 78.2% at 50° F., about 49.3% at 70° F., about 11.8% at 80° F., about 7.3% at 92° F., and about 7.8% at 100° F. using A.O.C.S. Method Cd 16-81;
- a viscosity of about 32.9 cps at 100° F. and about 26.3 cps at 150° F.;
- a heat of fusion of about 121.6 mJ/mg;
- A Lovibond Color of about 8 Red/79 Yellow using a 1 inch column following A.O.C.S. Method Cc 13b-45; and
- essentially no crystals exceeding 8 u observed on microscopic examination under polarized light.

Low calorie triglycerides of this invention can also be advantageously employed in low fat spread and margarine products. Low, i.e., 20 to 60%, fat spreads can be prepared by emulsifying the fats of this invention with an aqueous phase. Preferred fat compositions for low fat spreads have an array of triglycerides bearing different chain length substituents. Especially advantageous fat formulations contain, for example, acetic and butyric acid short chain substituents and a long chain moieties derived from fats having a variety of chain lengths, such as cottonseed oil. Illustrative formulations are given in the Examples.

Shortening Fats

The low calorie triglycerides of this invention are also especially advantageous in shortening compositions. Preferred shortening fat embodiments contain at least two triglyceride species bearing long, saturated acid residues and propionic acid, butyric acid, mixtures of acetic and propionic acid, mixtures of acetic acid and butyric acid, mixtures of propionic acid and butyric acid or mixtures of acetic acid, propionic acid, and butyric acid residues. The mixtures can comprise triglycerides bearing a mixture of short residues or can comprise a blend of triglycerides bearing one species of short residue with triglycerides bearing another species of short residue.

Typical shortening fat compositions of the invention have the following solid fat index:

| Temperatures | Solids (%) |
|---|---|
| 50° F. | at least 25 |
| 70° F. | at least 20 |
| 80° F. | 10 to 50 |
| 92° F. | 5 to 30 |
| 100° F. | 0 to 15 |
| more narrowly the following | |
| 50° F. | at least 30 |
| 70° F. | at least 25 |
| 80° F. | 15 to 30 |
| 92° F. | 10 to 20 |
| 100° F. | 0 to 10 |

One embodiment contains R' groups derived from a mixture of acetic and propionic acid residues. For example, one shortening comprises a mixture of about 35% diacetyl stearin and about 65% dipropionyl stearin. Another comprises a 1:1 mixture of diacetyl stearin and dipropionyl stearin. Another comprises a 1:1 mixture of diacetyl stearin and dibutyryl stearin. Another is prepared by randomly interesterifying, using a reactant molar ratio of 1:11:1, triacetin, tripropionin, and hydrogenated canola, hydrogenated soybean oil, or tristearin, and then steam deodorizing.

Another embodiment contains acetic and butyric R' groups; another, acetic, butyric, and propionic. Yet another contains about 10 to about 25 weight percent propionic acid residues. Another has R' groups derived entirely from propionic acid. Another contains about 10 to about 30 weight percent butyric acid residues. Another especially suitable as a spray oil has R' groups derived entirely from butyric acid; one such is prepared by the interesterification of about 12 moles tributyrin and one mole of tristearin or hydrogenated canola.

An advantage of this invention is that the geometry, e.g., height and spread, of finished bakery products containing some preferred embodiments of the shortenings of this invention can be altered by varying the short chain moieties in the shortening component. Another advantage is that the texture of the finished product can be varied widely, for example, from a cake-like to a hard snap consistency, by changing the low calorie shortening component. A further advantage is that some bakery products containing the shortenings of this invention retain moisture.

One preferred shortening fat of the invention comprises at least 95% triglycerides bearing one long chain fatty acid residue derived from a fat containing at least 90% 18 carbon cr higher fatty acid residues hydrogenated to an I.V. value of 3 or less and two short chain residues, each selected from the group consisting of acetic and propionic acid residues in a molar ratio of 7 to 57, said fat being essentially trans-free using A.O.C.S. Method Cd 14-61 and beta crystal free and having the following physical properties:

- a Mettler Drop point of about 63.7° F. using A.O.C.S. Method Cc 18-80;
- a smoke point of about 275° F. using A.O.C.S. Method Cc 9a-48;
- a flash point of about 470° F. using A.O.C.S. Method 9a-48;

a fire point of about 495° F. using A.O.C.S. Method 91-48;

a congeal point of about 27.7° C. using A.O.C.S. Method Ca 14-59;

a specific gravity at 60° C. of about 0.9347 using A.O.C.S. Method Cc 10b-25;

a peroxide value of about 0.77 meq/kg using A.O.C.S. Method 8-53;

a refractive index at 60° C. of about 1.4398 using A.O.C.S. Method Cc 7-25;

a saponification value of about 337 using A.O.C.S. Method 3-25;

an oxidation stability using A.O.C.S. Method Cd 12-57 for at least 290 hours;

a free fatty acid value of about 0.45% using A.O.C.S. Method 5a-40;

an S.F.C. of about 68.1% at 50° F., about 43.0% at 70° F., about 5.1% at 80° F., about 3.8% at 92° F., and about 4.7% at 100° F. using A.O.C.S. Method Cd 16-81;

a viscosity of about 32.9 cps at 100° F. and about 19.7 cps at 150° F.;

a heat of fusion of about 86.9 mJ/mg;

A Lovibond Color of about 16 Red/70 Yellow using a 1 inch column following A.O.C.S. Method Cc 13b-45; and essentially no crystals exceeding 8 u observed on microscopic examination under polarized light.

Other products

The low calorie triglycerides of this invention may advantageously be used in whipped toppings and coffee creamers. Desirable SFI profile values for the fat phase of whipped topping mixes are in the following ranges:

| Temperatures | Solids (%) |
| --- | --- |
| 50° F. | at least 45 |
| 70° F. | at least 30 |
| 80° F. | 15 to 25 |
| 92° F. | 5 to 20 |
| 100° F. | 0 to 10 |

The triglycerides of this invention are also especially suitable in nut products, especially those having at least about 50%, preferably 65% or more of the nut oil removed and replaced with the low calorie fats. Other exemplary food products which can be improved by the use of the low calorie triglycerides of this invention are: baked foods, such as cookies, crackers, biscuits, cakes and the like which all contain at least a flour or starch component in addition to the low calorie triglycerides of this invention; snack products which are fried or coated with fat or oil and/or also contain at least a flour or starch component in addition to the low calorie triglycerides; emulsion products in addition to margarine products such as salad dressing and mayonnaise which all contain emulsions having a fat phase including the low calorie triglycerides and an aqueous phase; candies and confections which contain a sweetener such as sugar or aspartame in addition to the low-calorie triglycerides and a flavor such as chocolate; and dairy product substitutes which contain a dairy protein such as whey, casein or caseinate, or the like in addition to the low calorie triglycerides. The margarine products also typically contain a milk component and butter flavor, while the salad dressings will contain spices and the mayonnaise, egg. Among the baked products, cakes and cookies also contain sweeteners and the crackers typically contain salt.

EXAMPLES

The following examples are presented to further illustrate and explain the present invention and should not be taken as limiting in any regard. Unless otherwise indicated, all parts and percentages are by weight, and are based on the weight at the particular stage of the processing being described. Ratios of short to long (S/L) acid substituents are mole ratios.

Nuclear magnetic resonance (NMR) data reported are proton NMR data. NMR S/L ratios are determined as the ratio of intensities of the methyl ($-CH_3$) resonances for the short and long fatty acid groups, respectively, obtained by dividing the integral areas attributable to S components by the areas attributable to the L, and have experimental errors of 5 to 10%. In a typical NMR spectrum at 300 MegaHertz or higher, the long acid methyl resonance occurs farthest upfield, at ~0.9 ppm, as a triplet. The short acid methyl resonance is structure dependent and occurs at ~2.00 ppm (acetyl groups), ~1.15 ppm (propionyl groups) and ~0.95 ppm (butyryl groups).

Differential scanning calorimetry (DSC) is used to obtain information about the melting and crystallization behavior of reduced calorie triglycerides. A liquid sample is cooled from about 20° C. above its melting point to about 20° C. below, held at the final temperature, and then reheated to the initial temperature. Crystallization and melting thermograms are subjected to several analyses. The melting point(s) are taken as the peak minima (endothermic transition in the down direction of the chart plotting mW per unit time versus temperature) obtained in the heating cycle, and the crystallization temperature as the peak onset in the cooling cycle. Enthalpies of phase transitions are automatically calculated in mJoules/mg of sample by choosing the two temperature points of onset of melting and 100% melted. For compound mixtures prepared from natural oils, it is useful to calculate, by integration, a solid fat index in which the percent liquid portion of the sample is calculated for any temperature. As described hereinafter, this method is employed where A.O.C.S. Methods Cd 16-81 or Cd 10-57 are not used.

Example 1

Acetyl-distearoyl glyceride (sometimes commonly called acetyl distearin), which comprises a mixture of 1-acetyl-2, 3-distearoyl glyceride (SLL) and 2-acetyl- 1,3-distearoyl glyceride (LSL),

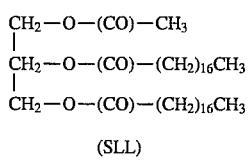

(SLL)

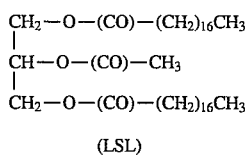

(LSL)

and which may be used as a component of the fat compositions of this invention, is prepared in this example.

One gram of distearin, obtained commercially from Sigma Chemical Co., is charged to a 100 mL round-bottomed flask equipped with a magnetic stir bar, a reflux condenser, a thermometer, and a heating mantle. To this is added an excess (15 mL) of acetic anhydride (95%, Aldrich Chemicals), and the mixture is heated to reflux with constant stirring for three hours. After cooling to ambient temperature, the mixture is transferred into a separatory funnel using 75 mL diethyl ether.

The solution is washed alternatively with 10% sodium bicarbonate and water until it is neutral to litmus. Finally, the sample is dried at 90° C. for one hour. Analysis of DSC (differential scanning calorimetry) data shows the sample to be 100% solid at 80° F., 98% solid at at 92° F., and solid at 100° F.

Example 2

Other component fats, namely, propionyl-distearoyl glyceride (sometimes commonly called propionyl distearin), a mixture of 1-propionyl-2,3-distearoyl glyceride and 2-propionyl-1,3-distearoyl glyceride, which have the following structures,

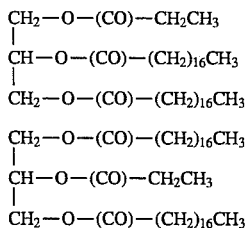

and butyryl-distearoyl glyceride (sometimes commonly called butyryl distearin), a mixture of 1-butyryl-2,3-distearoyl glyceride and 2-butyryl-1,3-distearoyl glyceride, which have the following structures,

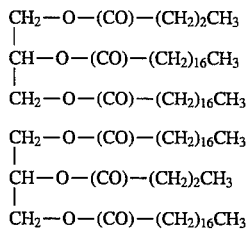

may be prepared by substituting propionic anhydride and butyric anhydride, respectively, for acetic anhydride in the esterification of distearin as outlined in Example 1 above.

Example 3

This example illustrates the preparation of another fat, diacetyl-stearoyl glycerol (sometimes commonly called stearoyl diacetin), a mixture of 1,2-diacetyl-3-stearoyl glyceride and 1,3-diacetyl-2-stearoyl glyceride, which have the following structures, respectively:

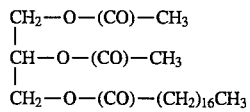

-continued

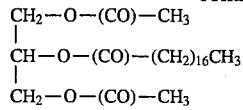

One gram of glycerol monostearin, obtained commercially from Spectrum Chemicals, is charged to a 100 mL round-bottomed flask equipped with a magnetic stir bar, a reflux condenser, a thermometer, and a heating mantle. An excess (15 mL) of acetic anhydride (obtained from Aldrich Chemicals) is added, and the mixture heated to reflux for three hours with constant stirring. After cooling to ambient temperature, the mixture is transferred to a separatory funnel using 75 mL diethyl ether.

The solution is washed alternately with 10% sodium bicarbonate and water until it is neutral to litmus and then dried at 90° C. for one hour to afford a mixture of triacylglyceride structures.

Example 4

This example illustrates alternative syntheses of acetyl-distearoyl glyceride prepared and illustrated in Example 1 above and diacetyl-stearoyl glyceride prepared and illustrated in Example 3 above.

To 90 mg (0.14 moles) 1,3-distearin is added 5 mL acetyl chloride, and the mixture is stirred and heated to 85° C. until all the acetyl chloride is reacted. An additional 2 mL acetyl chloride is added and the mixture is reheated to yield predominantly 2-acetyl-1,3-distearoyl glyceride.

A mixture of 2.1 g (0.01 mole) stearoyl chloride and 1.4 g (0.01 mole) monoacetin obtained from Kodak is heated to 85° C. for 2 hours. Another 4.0 g stearoyl chloride is added and the mixture is reheated to yield predominantly 1-acetyl-2,3-distearoyl glyceride.

To 100 mg (0.28 moles) monostearin is added about 5 mL acetyl chloride, and the mixture is stirred and heated to 80° C. in a reaction flask for an hour to yield predominantly 1,2-diacetyl-3-stearoyl glyceride.

Example 5

Other component fats, namely, dipropionyl-stearoyl glyceride, a mixture of 1,2-dipropionyl-3-stearoyl glyceride and 1,3-dipropionyl-2-stearoyl glyceride, which have the following structures, respectively,

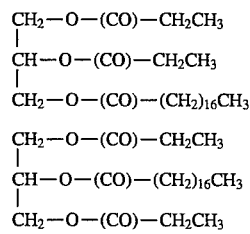

and dibutyryl-stearoyl glycerol, a mixture of 1,2-dibutyryl-3-stearoyl glyceride and 1,3-dibutyryl-2-stearoyl glyceride, which have the following structures

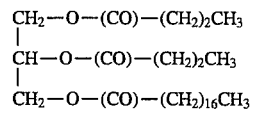

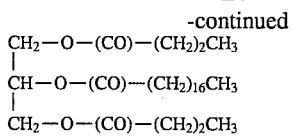

may be prepared by substituting propionic anhydride and butyric anhydride, respectively, for acetic anhydride in the esterification of monostearin as outlined in Example 3 above.

Example 6

In this example, 1,2-dibutyryl-3-stearoyl glyceride (depicted above), a triglyceride component that may be employed in the mixtures of this invention, is prepared using an alternate synthetic route employing tributyrin and methyl stearate (Akoh, C. C., and Swanson, B. G., *J. Amer. Oil Chem. Soc.* 66: 1581–1587 (1989)).

A 250-mL, 3-neck flask fitted with a temperature probe, stopper, and vacuum outlet is charged with 52 g (~0.17 moles) of tributyrin and 52 g (~0.17 mole) methyl stearate. The mixture is warmed to 48°–50° C. Sodium (2.3 g) is heated in 100 mL xylene to remove sodium oxides and then added to the warmed mixture, causing vigorous bubbling. Vacuum is applied, and the mixture is gradually heated to 110° C. The solution becomes yellow, then amber, and, after about 40 minutes, very viscous. Heat is removed, and the reaction mixture is cooled and extracted with hexane (100 mL), ethyl acetate (200 mL), acetic acid (5 mL), hydrochloric acid (10 mL), and (200 mL) water (200 mL). The organic layer is washed twice with salt water (100 mL), dried over magnesium sulfate, filtered, and concentrated to obtain a clear, pale yellow oil. The product is purified on a silica gel column eluted with hexane and hexane/ethyl acetate (20:1, v/v).

Example 7

A reduced calorie triglyceride fat mixture of 1-acetyl-2,3-distearoyl glyceride, 1,3-diacetyl-2-stearoyl glyceride 2-acetyl-1,3-distearoyl glyceride, and 1,2-diacetyl-3-stearoyl glyceride is prepared in this example.

One gram of glycerol monostearin and distearin, obtained commercially from Stephan Chemicals is charged to a 100 mL round-bottomed flask equipped with a magnetic stir bar, a reflux condenser, a thermometer, and a healing mantle. An excess of acetic anhydride (15 mL, Aldrich Chemicals) is added, and the mixture heated to reflux with constant stirring for three hours. After cooling to ambient temperature, the mixture is transferred to a separatory funnel using 75 mL diethyl ester.

The solution is washed alternately with 10% sodium bicarbonate and water until it is neutral to litmus, and then dried at 90° C. for one hour to give a mixed triacylglyceride composition.

Example 8

Other reduced calorie fat mixtures, such as (i) dipropionyl-stearoyl glyceride and propionyl-distearoyl glyceride, a mixture of 1,2-dipropionyl-3-stearoyl glyceride, 1,3-dipropionyl-2-stearoyl glyceride, 1-propionyl-2,3 -distearoyl glyceride, and 2-propionyl-1,3-distearoyl glyceride, and (ii) dibutyryl-stearoyl glyceride and butyryl-distearoyl glyceride, a mixture of 1,2-dibutyryl- 3-stearoyl glyceride, 1,3-dibutyryl-2-stearoyl glyceride, 1-butyryl-2,3-distearoyl glyceride, and 2-butyryl-1,3 -distearoyl glyceride, may be prepared by substituting propionic anhydride and butyric anhydride, respectively, for acetic anhydride in the esterification of monostearin and distearin as outlined in Example 7 above.

Example 9

In this example, a triglyceride mixture comprising acetyl-stearoyl glycerides of the formulae

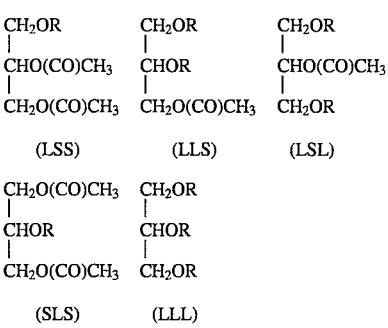

where the R groups are predominantly —(CO)(CH$_2$)$_{16}$CH$_3$ is prepared.

A 3-L, 3-neck reaction flask equipped with a heating mantle, stirrer, thermometer and reflux condenser is charged with 1140 g technical grade (~40%) monostearin obtained commercially from Stephan, Maywood, N.J. S.F.C. (supercritical fluid chromatography, a quantitative method more completely described in Example 21 below) analysis of the starting material reveals 50% monoglyceride, 27% diglyceride and 23% triglyceride. The starting material is melted, 360 g acetic anhydride (~98% pure, obtained from Aldrich Chemicals) is added, and the mixture is refluxed under vacuum for 12 hours. During the course of the reaction, 195 g of clear acetic acid is removed.

The golden honey-colored product is purified using a falling-film still at 180° C., >1 mm Hg to yield a light, soft solid. This is further purified using steam deodorization at 180° C., >1 mm Hg to yield 1113 g (86.3%) bright yellow solid having a capillary melting point of 53° C. NMR analysis shows an S/L ratio of 0.9. S.F.C. analysis (more fully described in Example 21 below) shows 50% of the total composition to comprise SSL/SLS, 35% LSL/LLS, and 8.4% LLL (with 0.5% monoglycerides and 5.2% diglycerides).

Example 10

In this example, a propionyl-stearoyl glyceride mixture comprising LSS, SLS, LLS, LSL, and LLL components having the formulae

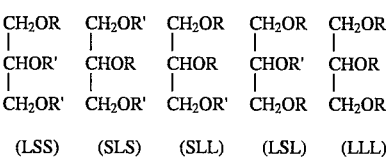

where

R' is —(CO)—CH$_2$CH$_3$ and

R is —(CO)(CH$_2$)$_{16}$CH$_3$ is prepared.

A 3-L, 3-neck reaction flask equipped with a heating mantle, stirrer, thermometer and reflux condenser is charged with 1110 g technical grade monostearin obtained commercially from Stephan (which contains mono-, di- and triglycerides as described in Example 9 above). The starting material is melted, 437 g propionic anhydride (~99% pure, obtained from Aldrich Chemicals) is added, and the mixture is refluxed at 160° C. for about 15 hours. The mixture is then distilled at 180° C. <100 mm Hg to remove propionic acid.

The product is then purified using a falling-film still at 180° C. and deodorized at <1 mm Hg, 50 mL H$_2$O, 170° C. to yield 1171 g (90.8%) of a soft solid having a capillary melting point of 54° C. NMR analysis shows the S/L ratio is 0.9. S.F.C. analysis (more fully described in Example 21 below) shows the final product contains 55% SSL/SLS, 33% LSL/LLS, and 8.2% LLL (with the remainder comprising 0.5% monoglyceride and 3.3% diglyceride).

Example 11

This example describes the preparation of another propionyl-stearoyl glyceride mixture like the one described in Example 10 above, except that different proportions of SSL, SLS, LLS, LSL, and LLL components are formed.

A 3-L 3-neck reaction flask equipped with a heating mantle, stirrer, thermometer and reflux condenser is charged with 914 g technical grade monostearin obtained commercially from EM Chemicals (Lot # 3006101). S.F.C. analysis of the starting material reveals 54.2% monoglycerides, 37.7% diglycerides and 8% triglycerides. The starting material is melted, 670 g propionic anhydride (~99% pure, obtained from Aldrich Chemicals) is added, and the mixture is refluxed at 180° C. for 12 hours. The mixture is then distilled at 25 mm Hg to remove propionic acid.

The product is then purified using a falling-film still at 180° C., <1 mm Hg and deodorized at 0.5 mm Hg, 45 mL H$_2$O, 180° C. to yield 924 g (77%) of a brown soft solid. NMR analysis shows the final product to have an S/L ratio of 1.2.

Example 12

This example describes an alternate preparation of dipropionyl-stearoyl glyceride (depicted in Example 4 above and as SSL and SLS in Examples 10 and 11 above).

A 3-L 3-neck reaction flask equipped with a heating mantle, stirrer, thermometer and reflux condenser is charged with 915 g monostearin obtained commercially from Spectrum Chemicals (≥90% pure, Lot # EF027). The starting material is melted, 697 g propionic anhydride (~99% pure, obtained from Aldrich Chemicals) is added, and the mixture is refluxed for 18 hours. The mixture is then distilled at <100 mm Hg, 180° C. to remove propionic acid.

The product is purified using a falling film still at 180° C., <1 mm Hg, and deodorized at 0.5 mm Hg, 50 mL H$_2$O, 180° C. to yield 1074 g (89.5%) of a clear orange liquid. NMR analysis shows the S/L ratio is 2.1. Analysis of DSC data shows 85% solids at 50° F., 56% solids at 70° F., 8% solids at 80° F., and 0% solids at 92° F.

Example 13

This example describes an alternate preparation of dibutyryl-stearoyl glyceride, SLS/SSL triglyceride mixture components depicted in Example 5 above.

A distearin starting material is first prepared. A 3-L, 2-neck reaction flask equipped with a heating mantle, thermometer, stirrer, and reflux condenser is charged with 248 g stearic anhydride (0.45 moles, obtained from Aldrich) and 37 g glycidol (0.5 moles). The mixture is stirred and heated to 95°–100° C. for 3 hours, 3.2 g tetraethylammonium bromide is added, and the is mixture stirred and heated for another 3 hours at 100°–105° C. DL-2-amino-1-propanol (2.4 g) is added and the flask is cooled until it solidifies (~65° C). The reaction flask is placed in a 60°–65° C. oven, held for 48 hours, and then heated to melt the product for transfer into a 4-L beaker. The product is crystallized from acetone, washed and dried. A 85% yield of a >93% pure product is obtained.

A 3-L, 3-neck reaction flask equipped with a heating mantle, stirrer, thermometer and reflux condenser is charged with 530 g of the distearin starting material. This is melted, 144 g butyric anhydride (~99% pure, obtained from Aldrich Chemicals) is added, and the mixture is refluxed at 180° C. for 8.5 hours. The mixture is distilled at <100 mm Hg, 200° C. to remove butyric acid.

The product is purified using a falling-film still at 180° C., <1 mm Hg and steam deodorized at 0.35 mm Hg, 180° C. to yield 545 g (91%) of a light brown solid having a capillary melting point of 37° to 38° C. NMR analysis shows the S/L ratio is 0.6.

Example 14

In this example, a butyryl-stearoyl glyceride mixture comprising LSS, SLS, LLS, LSL, and LLL components having the formulae

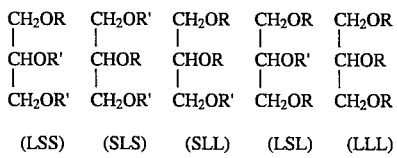

where

R' is —(CO)—(CH$_2$)$_2$CH$_3$ and

R is —(CO)(CH$_2$)$_{16}$CH$_3$ is prepared.

A 3-L, 3-neck reaction flask equipped with a heating mantle, stirrer, thermometer and reflux condenser is charged with 1078 g technical grade (~40%) monostearin obtained commercially from Stephan (which contains mono-, di- and tristearin as described in Example 9 above). The starting material is melted, 507 g butyric anhydride (~97% pure, obtained from Aldrich Chemicals) is added, and the mixture is refluxed at 175° C. for about 15 hours. The mixture is then distilled to remove butyric acid.

The product is then purified using a falling-film still at 120° C., <1 mm Hg, and steam deodorized at <1 mm Hg, 50 mL H$_2$O, 180° C. to yield 1173 g (90.8%) of a soft beige final product having a capillary melting point of 45° C. NMR analysis shows an S/L ratio of 0.9. S.F.C. analysis (more fully described in Example 21 below) shows 56.4% SSL/SLS, 30% LSL/LLS, and 8.7% LLL (with 4.9% diglycerides).

Example 15

This example describes the preparation of another butyryl-stearoyl glyceride mixture like the one described in Example 14 above.

A 3-L, 3-neck reaction flask equipped with a heating mantle, stirrer, thermometer and reflux condenser is charged with 864 g technical grade monostearin obtained commercially from EM Chemicals (Lot # 3006101, described in Example 11 above). The starting material is melted, 770 g butyric anhydride (~99% pure, obtained from Aldrich Chemicals) is added, and the mixture is refluxed at 180° C. for about 12 hours. The mixture is then distilled to remove butyric acid.

The liquid product is purified using a falling-film still and steam deodorized at 0.35 mm Hg, 40 mL H$_2$O, 180° C. to yield 924 g (77%) of a brown soft solid. NMR analysis shows an S/L ratio of 1.2.

Example 16

This example describes the preparation of another butyryl-stearoyl glyceride mixture like the ones described in Examples 13 and 14 above.

A 3-L, 3-neck reaction flask equipped with a heating mantle, stirrer, thermometer and reflux condenser is charged with 864 g monostearin obtained commercially from Spectrum Chemicals (≧90% pure, Lot # EF027). The starting material is melted, 770 g butyric anhydride (~97% pure, obtained from Aldrich Chemicals) is added, and the mixture is refluxed at 155° C. for about 16 hours. The deep orange-red mixture is then distilled to remove butyric acid.

The milky golden liquid product is purified using a falling-film still and steam deodorized at <1 mm Hg, 50 mL H$_2$O, 180° C. to yield 1041 g (87%) of a yellow golden liquid having a white precipitate. NMR analysis shows an S/L ratio of 2.0. Analysis of DSC data shows 86% solids at 50° F. 13% solids at 70° F., and 0% solids at 80° F.

Example 17

In this example, a blend of predominantly LSL/LLS propionyl-stearoyl glyceride and butyryl-stearoyl glyceride (depicted in Examples 10 and 14 above) is prepared.

A propionyl-stearoyl glyceride component is prepared by reacting a 1:1 molar ratio of distearin with propionic anhydride. A 2-L, 2-neck flask equipped with a thermometer, reflux condenser, heating mantle and stirrer is charged with 367 g distearin, which is melted prior to adding 76 g propionic anhydride. The mixture is refluxed at 125° C. for ~5 hours, left to stand overnight at room temperature, and refluxed with stirring at 80° C. for 6 hours. The mixture is distilled to yield a solid crude product that is dissolved in hexane and washed with water until neutral. Hexane is removed in vacuuo and the off-white product solid, dried. The yield is 374 g (93%).

A butyryl-stearoyl glyceride component is prepared by reacting distearin with butyric anhydride (~99% pure, obtained from Aldrich). A 3-L, 3-neck flask equipped with a thermometer, reflux condenser, heating mantle and stirrer is charged with 720 g distearin, which is half melted prior to adding 204 mL butyric anhydride. The mixture is heated for ~2½ hours at 85° C., left to stand without heat for two days, and refluxed at 85° C. for 8 hours. The mixture is distilled twice at 1 mm Hg to yield 743 g (93%) of a hard, light brown solid.

The butyryl-stearoyl glyceride component (650 g) is mixed with the propionyl-stearoyl glyceride component (350 g) in a 2-L beaker and heated. The blend is steam deodorized at 180° C., 1 mm Hg, 30 mL H$_2$O to yield a product having a melting point of 37° to 39° C. and an NMR S/L ratio of 0.6.

Example 18

In this example, another blend of propionyl-stearoyl glyceride and butyryl-stearoyl glyceride similar to the one prepared in Example 17 above, but having a different array of components, is prepared.

A propionyl-stearoyl glyceride component is prepared by reacting distearin with propionic anhydride. A 3-L, 3-neck flask equipped with a stirrer, heating mantle, thermometer, and reflux condenser is charged with 500 g of a distearin prepared as set out in Example 13, except that no 2-amino-propanol and no recrystallization steps are made. NMR analysis indicates the starting material comprises 90% distearin, 8% tristearain, and 2% monostearin. This is melted prior to adding 111 g propionic anhydride (Aldrich). The mixture is refluxed 14 hours, distilled, and purified in a falling-film still (<1 mm Hg, 180° C.). The final product, 545 g (95% yield), is a dark brown solid having a melting point of 58° to 60° C.

A butyryl-stearoyl glyceride component is prepared by reacting distearin with butyric anhydride. A 2-L, 3-neck flask equipped with a stirrer, heating mantle, thermometer, and reflux condenser is charged with 562 g of the distearin employed in the propionyl-stearin synthesis outlined above. This is melted prior to adding 150 g butyric anhydride (Aldrich). The mixture is refluxed at reduced pressure 2 hours, distilled, and purified in a falling-film still (<1 mm Hg, 180° C.). The final product, 605 g (96% yield), is a dark brown solid which NMR analysis shows to have a triglyceride content of 96%.

The propionyl-stearcyi glyceride component (387 g) is melted with the butyryl-stearoyl glyceride component (721 g) and stirred well. The blend is purified using a steam deodorizer at 0.6 mm Hg, 175° C., 35 mL water to yield a product comprising 29% propionyl-stearoyl glyceride and 61% butyryl-stearoyl glyceride having an NMR S/L ratio of 0.8.

Example 19

In this example, a blend of predominantly SSL and SLS diacetyl-stearoyl glyceride and dipropionyl-stearoyl glyceride components (depicted in Examples 3 and 5 above) is prepared.

An diacetyl-stearoyl glyceride component is prepared by reacting monostearin with acetic anhydride. A 2-L, 3-neck flask equipped with a stirrer, heating mantle, thermometer, and reflux condenser is charged with 406 g monostearin obtained from Spectrum Chemicals. This is melted prior to addition of acetic anhydride (Aldrich), and the mixture is refluxed at 140° C. for 2 hours, held overnight without heat, and refluxed for 3 more hours. Acetic acid is distilled off, and the product purified in a falling-film still (1 mm Hg, 180° C.) to yield 438 g (83%) of a golden yellow solid, which NMR show to contain triglycerides only.

A dipropionyl-stearoyl glyceride component is prepared by reacting monostearin with propionic anhydride. A 3-L, 3-neck flask equipped with a stirrer, heating mantle, thermometer, and reflux condenser is charged with 771 g monostearin obtained from Spectrum Chemicals. This is melted and 552 g propionic anhydride (Aldrich) is added. The mixture is refluxed 3.5 hours, held overnight without heating, and refluxed 5 more hours. The product is distilled and purified in a falling-film still (<1 mm Hg) to yield 935 g (94%) of a clear, golden yellow liquid.

The diacetyl-stearoyl glyceride component (421 g) and the dipropionyl-stearoyl glyceride component (780) are melted together, mixed well, and steam deodorized at 0.6 mm Hg, 168° C., 40 mL H$_2$O. The final blend comprises 31% diacetyl-stearin and 69% dipropionyl-stearin, and has an NMR S/L ratio of 1.8.

Example 20

In this example, reduced calorie fat mixtures are prepared by interesterifying hydrogenated canola (refined, low erucic rapeseed oil containing 4% palmitic acid, hydrogenated at 180° C. and 60 lbs hydrogen until the Iodine Value (IV) is ≦3) with tributyrin (obtained commercially from Eastman Kodak). A Mettler dropping point (M.D.P.) is determined for each mixture using a Mettler Thermosystem FP 800 following A.O.C.S. Method Cc 18-80 (1989). A solid fat index (S.F.I.) is obtained using A.O.C.S. Method Cd 10-57 (1989). Each mixture is subjected to proton nuclear magnetic resonance (NMR) spectroscopy; integration of the intensities of the various groups gives an estimate of the molar ratio of short (in this case, butyric) to long acids (S/L) present.

One molar equivalent hydrogenated canola (899 g) and 2 to 4.5 molar equivalents tributyrin are interesterified in the presence of 0.2 to 0.3% sodium methoxide by heating to ~110° C. with agitation under a vacuum for about half an hour until color develops. (The M.D.P. may be checked at this time, and the reaction continued if the M.D.P. has not dropped sufficiently.) Phosphoric acid (~0.2 to ~0.5%, at least twice the amount of sodium methoxide) is added to stop each reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for ½ to 1 hour at 110° C. The products are cooled to 80° C., filtered, bleached, and steam deodorized at 210° C. for 2 to 3 hours.

Using this procedure, a 1:25 molar reactant ratio of hydrogenated canola to tributyrin yields a liquid product having a M.D.P. of 18.6° C. and an NMR S/L of 2.0. Conversely, a 1:0.5 molar ratio yields a waxy product having a M.D.P. of 63.0° C. and an NMR S/L of 0.5; similarly, a 1:1 molar ratio of hydrogenated canola to tributyrin yields a product having a M.D.P. of 57.9° C. and an NMR S/L of 0.8. Using intermediate reactant ratios, the following triglyceride mixtures are obtained:

| Hydrogenated Canola:Tributyrin Reactant Molar Ratio | | | | | | | | |
|---|---|---|---|---|---|---|---|---|
| | | 1:2 | 1:2.5 | 1:3 | 1:3.5 | 1:4 | 1:4.5 | 1:12 |
| M.D.P., | °C. | 35.1 | 31.8 | 30.4 | 28.7 | 27.5 | 26.6 | 22.1 |
| S.F.I. | 50° F. | 68.8 | 69.5 | 66.8 | 63.6 | 63.8 | 63.4 | 54.3 |
| | 70° F. | 52.3 | 53.6 | 39.6 | 33.1 | 29.8 | 24.7 | 3.8 |
| | 80° F. | 24.0 | 23.7 | 8.8 | 4.7 | 3.9 | 2.1 | 0.0 |
| | 92° F. | 10.0 | 9.2 | 4.3 | 3.2 | 2.3 | 1.6 | 0.0 |
| | 100° F. | 9.2 | 8.8 | 4.0 | 2.6 | 0.0 | 0.0 | |
| NMR S/L | | 1.2 | 1.2 | 1.3 | 1.4 | 1.5 | 1.4 | 1.8 |

Example 21

This example illustrates a method of analyzing hydrogenated canola/tributyrin triglyceride mixtures prepared in Example 20 using supercritical fluid chromatography (S.F.C.) to separate and quantify the mixture components.

After filtering through a 0.45 micron filter, 0.1 ul of a 30 to 50 mg/ml sample is injected onto a 1×100 mm Deltabond Cyano™ column from Keystone Scientific in a Suprex Model 200A S.F.C. having an S.F.C.- grade carbon dioxide mobile phase and an oven temperature of 125° C. A linear pressure gradient of 100 to 300 atmospheres is applied over a course of 20 minutes (i.e., 10 atm/min), followed by a hold at 300 atmospheres for 10 minutes. A flame ionization detector at 400° C. detects emerging mixture components run against an internal standard of methyl tetradecanoate (10 to 12 mg/mL) in methylene chloride. External standards of mono, di, and tristearin (~10 mg/mL each) are run under identical conditions. Using these peak areas, the peak areas of the sample are normalized, added together, and divided by the total to obtain the following percentages of LSS & SLS, LLS & LSL, and LLL in the mixtures:

| Hydrogenated Canola:Tributyrin Reactant Molar Ratio | | | | | | | | |
|---|---|---|---|---|---|---|---|---|
| | 1:0.5 | 1:1 | 1.2 | 1:2.5 | 1:3 | 1:3.5 | 1.4 | 1:4. |
| % LSS/SLS | 17.0 | 39.2 | 57.2 | 67.2 | 69.4 | 73.2 | 78.1 | 80.2 |
| % LLS/LSL | 38.5 | 43.8 | 34.7 | 28.8 | 27.1 | 24.0 | 20.5 | 18.4 |
| % LLL | 44.5 | 17.1 | 8.1 | 4.0 | 3.4 | 2.7 | 1.4 | 1.4 |

The mixtures prepared in Example 20 thus include, after purification, compounds of the formula

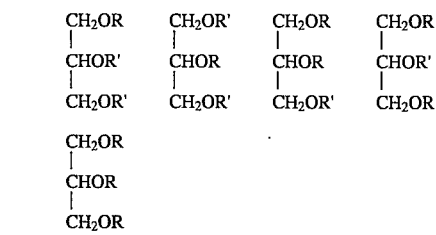

where

R' is —(CO)—(CH$_2$)$_2$CH$_3$ and

R is derived from hydrogenated canola oil

Example 22

In this example, reduced calorie fat mixtures are prepared by interesterifying one mole hydrogenated canola (obtained as described in Example 20) with 2.5, 3.5, or 12 moles tripromionin (obtained commercially from Pfaltz & Bauer).

Using the preparative and analytical procedures outlined in Example 20, the following M.D.P., S.F.I., and NMR S/L data on the products are obtained:

| Hydrogenated Canola:Tripropionin Reactant Molar Ratio | | | | |
|---|---|---|---|---|
| | | 1:2.5 | 1:3.5 | 1:12 |
| M.D.P., | °C. | 34.4 | 33.5 | 27.2 |
| S.F.I. | 50° F. | 70.6 | 61.7 | 54.9 |
| | 70° F. | 66.1 | 56.5 | 32.2 |
| | 80° F. | 51.2 | 35.5 | 0.8 |
| | 92° F. | 7.3 | 0.0 | 0.0 |
| | 100° F. | 4.3 | 0.0 | 0.0 |
| NMR S/L | | 1.2 | 1.4 | 2.2 |

Example 23

Reduced calorie fat mixtures are prepared as described in Example 22, except that the interesterification mixture contains hydrogenated canola (obtained as described in Example 20) with both tripropionin (1.25, 1.75, and 6 moles to 1 mole hydrogenated canola) and tributyrin (in the same proportions).

Using the preparative and analytical procedures outlined in Example 22, the following M.D.P., S.F.I., and NMR S/L data on the products are obtained:

| Hydrogenated Canola:Tributyrin:Tripropionin Reactant Molar Ratio | | | | |
|---|---|---|---|---|
| | | 1:1.25:1.25 | 1:1.75:1.75 | 1:6:6 |
| M.D.P., | °C. | 32.5 | 30.0 | 24.4 |
| S.F.I. | 50° F. | 67.7 | 65.0 | 51.7 |
| | 70° F. | 54.0 | 44.6 | 13.8 |
| | 80° F. | 28.1 | 16.6 | 0.0 |
| | 92° F. | 4.7 | 1.4 | 0.0 |
| | 100° F. | 4.4 | 2.3 | 0.0 |
| NMR S/L | | 1.3 | 1.5 | 2.1 |

Example 24

Reduced calorie fat mixtures are prepared as described in Examples 20 and 23, except that the interesterification mixture contains hydrogenated canola with both tripropionin (1.25 moles, 2.25 moles and 6 moles per mole hydrogenated canola) and triacetin (in the same proportions), the reaction temperature is 120° to 125° C., and 0.5% sodium methoxide is employed.

Using the preparative and analytical procedures outlined in Example 22, the following M.D.P. and S.F.I. data on the products are obtained:

| Hydrogenated Canola:Tripropionin:Triacetin Reactant Molar Ratio | | | | |
|---|---|---|---|---|
| | | 1:1.25:1.25 | 1:2.25:2.25 | 1:6:6 |
| M.D.P., | °C. | 36.8 | 33.8 | 31.4 |
| S.F.I. | 50° F. | 71.4 | 69.8 | 54.8 |
| | 70° F. | 69.8 | 56.0 | 34.2 |
| | 80° F. | 64.3 | 1.5 | 0.0 |
| | 92° F. | 23.0 | 0.0 | 0.0 |
| | 100° F. | 0.2 | 0.0 | 0.0 |
| NMR S/L | | 1.3 | 1.6 | 2.1 |

Example 25

Reduced calorie fat mixtures are prepared as described in Examples 20 and 23, except that the interesterification mixture contains hydrogenated canola (denoted below as "H-Canola") with triacetin, tripropionin, and tributyrin (in proportions set out below).

Using the preparative and analytical procedures outlined in Example 22, the following M.D.P. and S.F.I. data on the products are obtained:

| H-Canola:Triacetin:Tripropionin:Tributyrin Molar Reactant Ratio | | | | |
|---|---|---|---|---|
| | | 1:0.5:1.0:1.0 | 1:0.7:1.4:1.4 | 1:2:4:4.8:4.8 |
| M.D.P., | °C. | 35.0 | 31.3 | 26.8 |
| S.F.I. | 50° F. | 68.6 | 67.8 | 63.3 |
| | 70° F. | 63.2 | 56.5 | 36.1 |
| | 80° F. | 42.5 | 29.6 | 1.0 |
| | 92° F. | 4.6 | 0.0 | 0.0 |
| | 100° F. | 4.6 | 0.0 | 0.0 |
| NMR S/L | | 1.4 | 1.6 | 2.1 |

Example 26

This example illustrates how the triglyceride mixtures of this invention are screened for caloric availability by a carefully controlled in vivo animal feeding study.

An experimental relationship between oil calories ingested and animal body weight gain is established by monitoring the body weight gain associated with consumption of a nutritionally balanced diet containing varying concentrations of a reference substance such as corn oil which has a known caloric availability. Correlations between total calories ingested and body weight gain are excellent (r=0.99).

Caloric availability of an unknown substance is evaluated by substituting a specific weight of the unknown substance for the reference substance and observing the body weight gain. The gain in body weight is equated to a total number of calories using the correlation previously established for the reference data. The estimated number of calories ingested are divided by the weight of unknown substance to give the apparent calories metabolized per gram for the unknown substance.

The test animals are weakling male Sprague-Dawley rats, weighing approximately 50 to 60 g prior to acclimation. After acclimation for 3 to 10 days, the test duration is 14 days. The dietary requirements are established by observing the actual feed consumption of animals provided with unlimited feed. All diets are prepared to contain 50% of the established dietary requirements plus any supplements of reference or unknown substances. In all tests so designed the test animals are maintained in very good health.

The animals are housed singly in suspended wire mesh cages which conform to the size recommendatins in the *Guide for the Care and Use of Laboratory Animals*, Department of Health, Education and Welfare, National Institute of Health Bulletin No. 78.23. Litter paper is changed at least three times a week. The animal room is temperature controlled, with a 12-hour light/dark cycle, and kept clean and vermin free. Water is provided ad-libitum.

There are ten animals per group. The test feeds are NIH 07 Open Formula Rodent Chow diets manufactured by Zeigler Bros., obtained as pellets or meal. Fortified diets employ 0.2% AIN-76A vitamin pre-mix obtained from Teklad. Weight gains are measured at days 0, 3, 7, 10, and 14.

The test groups are as follows:

| Group | Test Diet | Feeding Regimen |
|---|---|---|
| 1 | NIH-07 | Ad-libitum |
| 2 | NIH-07 | Pair Fed 50% of Gp. 1 |
| 3 | As Gp. 2 + 7% corn oil | Pair Fed 50% of Gp. 1 |
| 4 | As Gp. 2 + 14% corn oil | Pair Fed 50% of Gp. 1 |
| 5 | As Gp. 2 + 21% corn oil | Pair Fed 50% of Gp. 1 |

Rats were fed a diet of 21% triglyceride test substances prepared as described in the above Examples as test compounds under the foregoing procedure, and their weight gains were determined. Based upon the base line corn oil control data, and the data from the test substances, the following caloric availability data (expressed as kcal/gram) were determined:

| Low Calorie Triglycerides | kcal/g |
|---|---|
| Example 9 Acetyl-stearoyl Glycerides (S/L = 0.9) | 3.9 |
| Example 10 Propionyl-stearoyl Glycerides (S/L = 0.9) | 3.9 |
| Example 11 Propionyl-stearoyl Glycerides (S/L = 1.3) | 4.4 |
| Example 12 Propionyl-stearoyl Glycerides (S/L = 2.0) | 4.1 |
| Example 14 Butyryl-stearoyl Glycerides (S/L = 0.9) | 4.0 |
| Example 15 Butyryl-stearoyl Glycerides (S/L = 1.2) | 4.4 |

-continued

| Low Calorie Triglycerides | kcal/g |
|---|---|
| Example 16 Butyryl-stearoyl Glycerides (S/L = 1.9) | 4.2 |
| Examnle 17 Butyryl/propionyl-stearoyl Glycerides | 3.1 |
| Example 18 Butyryl/propionyl-stearoyl Glycerides | 1.7 |
| Example 19 Acetyl/propionyl-stearoyl Glycerides | 4.8 |
| Example 20 1:1 Hydrogenated Canola/Tributyrin | 3.6 |
| Example 20 1:2 Hydrogenated Canola/Tributyrin | 3.9 |
| Example 20 1:2.5 Hydrogenated Canola/Tributyrin | 3.9 |
| Example 20 1:3 Hydrogenated Canola/Tributyrin | 3.8 |
| Example 20 1:3.5 Hydrogenated Canola/Tributyrin | 3.8 |

Example 27

This example describes feeding studies using the method described in Example 26 above, except that rats were fed a diet of 21%, 15%, 10% and 5% triglyceride test substance. The test substance is a triglyceride mixture obtained by the interesterification of hydrogenated canola and tributytin in a 1:2.5 molar ratio as described in Example 20.

Caloric availability is estimated by comparing weight gain of rapidly growing male rats fed corn oil compared to weight gain of rats fed the test oil.

To conduct the experiment, a group of 10 rats are fed NIH-07 open formula died ad libitum. This group is started on the diet one day ahead of all the others. Each day the feed consumption for the ad libitum group is determined.

All experimental groups receive 50% of the NIH-07 diet consumed on the previous day. The standard curve for growth is developed by supplementing the NIH-07 diets with various levels of corn oil (0, 5, 10, 15 and 21%). The mean body weight gain for each corn oil supplemented sample is regressed against the calories from corn oil (feed consumption * % corn oil * 9) for 0, 5, 10, and 15% corn oil to establish the equation of the standard curve. The 21% corn oil weight gain is dropped from the standard curve calculation because the response is not linear at that level (the animals being saturated with amount of fat in the diet). The weight gain for rats consuming test oil are compared to the standard curve, and calories are calculated using the formula:

$$\text{test oil kcal/g} = \frac{(\text{weight gain on test oil} - \text{intercept})}{(\text{standard curve slope} * \% \text{ test oil in diet})}$$

The following caloric availability are obtained:

| Dietary Level | kcal/g |
|---|---|
| 5% | 4.6[a] |
| 10% | 6.0[b] |
| 15% | 5.8[a] |
| 21% | 4.6%[c] |

Example 28

In this example, reduced calorie fat mixtures are prepared using the protocol described in Example 20 by interesterifying hydrogenated canola and tributyrin. With a 1:12 molar reactant ratio of hydrogenated canola to tributyrin, a product with an M.D.P. of 22.5° C. and an NMR S/L ratio of 1.8 was obtained; the S.F.I. is 50.7% at 50° F., 3.9% at 70° F., and 0% at 80%. Increasing the proportion of tributyrin to 1:25 yielded a product with an M.D.P. of 18.6° C. and an NMR S/L ratio of 2.0; the S.F.I. is 1.7% at 50° F., 2.6% at 70° F., and 0% at 80° F.

Example 29

In this example, reduced calorie fat mixtures are prepared using the protocol described in Example 20 by interesterifying one mole fully hydrogenated high erucic rapeseed oil (obtained from CSP) with 2.5, 4.0, or 12 moles tripropionin (obtained commercially from Pfaltz & Bauer). Using the preparative and analytical procedures outlined in Example 20, the following M.D.P., S.F.I., and NMR S/L data on the products are obtained:

| Hydrogenated Rapeseed:Tripropionin Reactant Molar Ratio | | | | |
|---|---|---|---|---|
| | | 1:2.5 | 1:4 | 1:12 |
| M.D.P., | °C. | 44.6 | 42.5 | 39.2 |
| S.F.I. | 50° F. | 79.3 | 76.7 | 68.7 |
| | 70° F. | 74.9 | 72.0 | 61.8 |
| | 80° F. | 73.6 | 68.9 | 52.8 |
| | 92° F. | 60.4 | 48.7 | 24.9 |
| | 100° F. | 38.7 | 25.0 | 3.5 |
| NMR S/L | | 1.2 | 1.5 | 1.9 |

Example 30

In this example, reduced calorie fat mixtures are prepared using the protocol described in Example 20 by interesterifying one mole fully hydrogenated menhaden fish oil (obtained from Zapata Hayne) with 2.5, 4.0, or 12 moles tripropionin (obtained commercially from Pfaltz & Bauer).

Using the preparative and analytical procedures outlined in Example 20, the following M.D.P., S.F.I., and NMR S/L data on the products are obtained:

| Hydrogenated Fish Oil:Tripropionin Reactant Molar Ratio | | | | |
|---|---|---|---|---|
| | | 1:2.5 | 1:4 | 1:12 |
| M.D.P., | °C. | 32.7 | 31.3 | 25.9 |
| S.F.I. | 50° F. | 60.5 | 55 | 40.6 |
| | 70° F. | 41.3 | 32.4 | 13.3 |
| | 80° F. | 22.2 | 12.3 | 0.2 |
| | 92° F. | 3.0 | 0.0 | 0.0 |
| | 100° F. | 0.3 | 0.0 | 0.0 |
| NMR S/L | | 1.1 | 1.4 | 2.0 |

Example 31

Using the procedure outlined in Example 20, tributyrin is interesterified with safflower oil obtained from Welch, Holme, and Clark. A liquid oil (having no solids at 50° F. to 100° F.) is obtained with oil to tributyrin reactant molar ratios of 1:2.5, 1:4, and 1:12.

Example 32

Using the procedure outlined in Example 20, tripropionin is interesterified with safflower oil. A liquid oil (having no solids at 50° to 100° F.) is obtained with oil to tributyrin reactant molar ratios of 1:2.5, 1:4, and 1:12.

Example 33

In this example, reduced calorie fat mixtures are prepared using the protocol described in Example 20 by interesterifying hydrogenated canola oil with tripropionin and safflower oil.

With a safflower:hydrogenated canola:tripropionin reactant molar ratio of 0.66:0.33:12, and oil with no solids at 50° to 100° F. is obtained. Using the preparative and analytical procedures outlined in Example 20, the following S.F.I. data on products prepared using other ratios are obtained:

| | Safflower:Hydrogenated Canola:Tripropionin Reactant Molar Ratio | | |
|---|---|---|---|
| S.F.I. | 0.33:0.66:2.5 | 0.33:0.66:12 | 0.66:0.33:2.5 |
| 50° F. | 24.1 | 16.0 | 1.5 |
| 70° F. | 4.7 | 0.2 | 0 |
| 80° F. | 1.2 | 0 | |
| 92° F. | 0.6 | | |
| 100° F. | 0 | | |

Example 34

Using the feeding study protocol set out in Example 26, rats were fed a diet of 21% triglyceride test substances prepared as described in the previous Examples as test compounds. As used herein, hydrogenated canola is abbreviated "H-Canola." Based upon the base line corn oil control data, and the data from the test substances, the following caloric availability data (expressed as kcal/gram) were calculated as described in Example 27:

| Low Calorie Triglycerides | kcal/g |
|---|---|
| Ex. 22 Hydrogenated Canola/Tripropionin (S/L = 1.2) | 4.7 |
| Ex. 22 Hydrogenated Canola/Tripropionin (S/L = 1.3) | 4.3 |
| Ex. 22 Hydrogenated Canola/Tripropionin (S/L = 2.2) | 4.7 |
| Ex. 23 H-Canola/Tripropionin/Tributyrin (S/L = 1.3) | 4.8 |
| Ex. 23 H-Canola/Tripropionin/Tributyrin (S/L = 1.3) | 4.8 |
| Ex. 23 H-Canola/Tripropionin/Tributyrin (S/L = 2.1) | 5.6 |
| Ex. 24 H-Canola/Triacetin/Tripropionin (S/L = 1.3) | 5.0 |
| Ex. 24 H-Canola/Triacetin/Tripropionin (S/L = 1.6) | 5.0 |
| Ex. 24 H-Canola/Triacetin/Tripropionin (S/L = 2.1) | 5.4 |
| Ex. 25 S/L 1.4 H-Canola/Triacetin/Tripropionin/Tributyrin | 5.2 |
| Ex. 25 S/L 1.6 H-Canola/Triacetin/Tripropionin/Tributyrin | 5.3 |
| Ex. 25 S/L 2.1 H-Canola/Triacetin/Tripropionin/Tributyrin | 5.7 |
| Ex. 28 1:12 Hydrogenated Canola/Tributyrin (S/L = 1.8) | 5.2 |
| Ex. 28 1:25 Hydrogenated Canola/Tributyrin (S/L = 2.0) | 6.2 |
| Ex. 31 Safflower/Tributyrin (S/L = 0.9) | 6.7 |
| Ex. 31 Safflower/Tributyrin (S/L = 1.1) | 6.6 |
| Ex. 31 Safflower/Tributyrin (S/L = 1.5) | 6.7 |
| Ex. 32 Safflower/Tripropionin (S/L = 1.2) | 6.9 |
| Ex. 32 Safflower/Tripropionin (S/L = 1.3) | 6.5 |
| Ex. 32 Safflower/Tripropionin (S/L = 2.0) | 6.0 |

Example 35

Using the feeding study protocol set cut in Example 26, rats were fed a diet of 10% triglyceride test substances prepared as described in the above Examples as test compounds. As used herein, hydrogenated canola is abbreviated "H-Canola" and hydrogenated high erucic rapeseed is abbreviated "H-Rapeseed." Based upon the base line corn oil control data, and the data from the test substances, the following caloric availability data (expressed as kcal/gram) were calculated as described in Example 27:

| Low Calorie Triglycerides | kcal/g |
|---|---|
| Example 20 1:2.5 H-Canola/Tributyrin and Triacetin | 3.3 |
| Example 20 1:2.5 H-Canola/Tributyrin and Triacetin | 3.9 |
| Example 29 H-Rapeseed/Tripropionin (S/L 1.2) | 3.8 |
| Example 29 H-Rapeseed/Tripropionin (S/L 1.5) | 4.1 |
| Example 29 H-Rapeseed/Tripropionin (S/L 1.9) | 5.7 |
| Example 30 Hydrogenated Fish Oil/Tripropionin (S/L 1.2) | 7.0 |
| Example 30 Hydrogenated Fish Oil/Tripropionin (S/L 1.4) | 7.4 |
| Example 30 Hydrogenated Fish Oil/Tripropionin (S/L 2.0) | 6.6 |
| Example 33 H-Canola/Safflower/Tripropionin (S/L 1.2) | 6.8 |
| Example 33 H-Canola/Safflower/Tripropionin (S/L 1.5) | 6.3 |
| Example 33 H-Canola/Safflower/Tripropionin (S/L 1.9) | 7.0 |
| Example 33 H-Canola/Safflower/Tripropionin (S/L 2.0) | 7.3 |

Example 36

Reduced calorie fat mixtures are prepared as described in Example 24, except that the interesterification mixture contains different proportions of hydrogenated canola (abbreviated "H-Canola"), tripropionin and triacetin. Using the preparative and analytical procedures outlined in Example 22, the following M.D.P. and S.F.I. data on the products are obtained:

| | H-Canola:Tripropionin:Triacetin Reactant Molar Ratio | |
|---|---|---|
| | | 1:1:11 | 1:11:1 |
| M.D.P., | °C. | 35.0 | 17.6 |
| S.F.I. | 50° F. | 64.4 | 55.0 |
| | 70° F. | 62.4 | 32.3 |
| | 80° F. | 58.7 | 7.4 |
| | 92° F. | 28.5 | 0.0 |
| | 100° F. | 0.4 | 0.0 |
| NMR S/L | | 1.8 | 1.8 |

Example 37

This example details the physical and chemical characterization of several reduced calorie triglyceride mixtures of this invention. Mixture A is prepared by the interesterification of 2.5 moles tributyrin with 1 mole hydrogenated canola as outlined in Example 20. The M.D.P. determined using A.O.C.S. Method Cc 18-80 is 30.9° C. and the S.F.I. obtained using A.O.C.S. Method Cd 10-57 shows 64.8% solids at 50° F., 38.7% at 70° F., 11.4% at 80° F., 4.9% at 92° F., and 5.2% at 100° F. Mixture B is prepared by the interesterification of 11 moles of triacetin and 1 mole tripropionin with 1 mole of hydrogenated canola, and mixture C is prepared by the interesterification of 1 mole of triacetin and 11 moles of tripropionin with 1 mole of hydrogenated canola as described in Example 36.

Viscosity is determined using a Haake viscometer, Rotovisco™ model RV12, with a M-500 measuring head consisting of a sensor system cup and a bell shaped rotor that are manually attached to a temperature vessel, then connected to a circulator and a temperature controlled waterbath. The method measures simple shear at two temperatures in the annular gap between two concentric cylinders. Continuous measurements of torque at zero up to 100 rpm are recorded on a chart from which viscosity of the liquid fat is calculated.

In the practice of viscosity determinations, the sample is melted (if not already liquid) and stirred thoroughly; the temperature during melting does not exceed the melting point of the sample by more than 10° C. For each temperature, the measured value (S) from the chart is read at the point that intercepts the curve at 50 rpm and the viscosity calculated using the following equation:

$$\text{viscosity (cp)} = \frac{G \times S}{n}$$

where

G is a constant instrument factor dependent on the torque of the measuring drive unit and the geometry of the sensor system (329 with the 4.0 Sensor System NV and the equipment described herein);

S is the measured value in scale units (from the chart); and n is the test speed in rpm at the measured value.

Fatty acids are determined using proton NMR as described heretofore, with results denoted in Table I following using the abbreviation "but." for butyric acid, "ac." for acetic acid, "pro." for propionic acid, and "st." for stearic acid. Short/long chain ratios are also determined using proton NMR, and the heats of fusion are determined using DSC as described heretofore. The other measurements follow A.O.C.S. methods as listed; Lovibond Color is assayed using a 1 inch column.

Using these analytical techniques the following data are obtained:

Example 38

This example compares the melting point behavior of monostearin derivatives as a function of chain length. Each derivative bears one stearic acid residue per molecule and two identical short or medium chain substituents.

Diacetyl monostearin is prepared by melting 968.22 g (2.7 moles) 1-glycerol-rac-monostearin obtained from Spectrum Chemicals (Lot # FC026) in a reaction flask equipped with a magnetic stirrer, heating mantle, thermometer, and reflux condenser prior to adding 578.85 g (5.67 moles) acetic anhydride (Aldrich Chemicals). The reaction flask is heated to 140° C. for 5 hours at atmospheric pressure, and the acetic acid side product is removed by vacuum distillation at 90 mm Hg, 95° C. The yield of distillate is quantitative. The dark brown waxy product is decolorized with activated charcoal and heptane for 10 hours; the carbon, removed with hot vacuum filtration; and heptane, removed by vacuum, yielding a golden yellow waxy product which is passed through a falling film still equipped with mesitylene as the boiling solvent (168° C., <1 mm Hg) and deodorized. The yield is 2.52 moles (92.9%) of a golden yellow wax having

TABLE I

| Properties | Method | Reduced Calorie Triglyceride Mixture | | |
|---|---|---|---|---|
| | | A | B | C |
| Fatty acids (mole %) | Proton NMR | 54% but. 46% st. | 51% ac. 13% pro. 36% st. | 7% ac. 57% pro. 36% st. |
| Short/Long Chain Ratio | Proton NMR | 1.2 | 1.8 | 1.8 |
| Mettler Drop Point | AOCS Method Cc 18-80 | 87.6° F. | 95.0° F. | 63.7° F. |
| Smoke Point | AOCS Method Cc 9a-48 | 310° F. | 260° F. | 275° F. |
| Flash Point | AOCS Method Cc 9a-48 | 480° F. | 470° F. | 470° F. |
| Fire Point | AOCS Method Cc 9a-48 | 510° F. | 495° F. | 495° F. |
| Peroxide Value | AOCS Method Cd 8-53 | 0.20 meq/kg | 0.45 meq/kg | 0.77 meq/kg |
| Free Fatty Acids | AOCS Method Ca 5a-40 | 0.23% | 0.78% | 0.45% |
| Congeal Point | AOCS Method Cc 14-59 | 30.6° C. | 33.8° C. | 27.7° C. |
| Sp. Gravity @ 60° C. | AOCS Method Cc 10-25 | 0.9097 | 0.9337 | 0.9347 |
| Refract Index @ 60° C. | AOCS Method Cc 7-25 | 1.4396 | 1.4385 | 1.4398 |
| Saponification Value | AOCS Method Cd 3-25 | 287 | 347 | 337 |
| AOM Oxidative Stability | AOCS Method Cd 12-57 | 295$^+$ hrs | 290$^+$ hrs | 290$^+$ hrs |
| Solid Fat Content @ 50° F. | AOCS Method Cd 16-81 | 78.2% | 82.1% | 68.1% |
| Solid Fat Content @ 70° F. | AOCS Method Cd 16-81 | 49.3% | 78.4% | 43.0% |
| Solid Fat Content @ 80° F. | AOCS Method Cd 16-81 | 11.8% | 71.7% | 5.1% |
| Solid Fat Content @ 92° F. | AOCS Method Cd 16-81 | 7.3% | 29.9% | 3.8% |
| Solid Fat Content @ 100° F. | AOCS Method Cd 16-81 | 7.8% | 4.9% | 4.7% |
| Viscosity @ 100° F. | Haake Viscometer | 32.9 cps | 35.1 cps | 32.9 cps |
| Viscosity @ 150° F. | Haake Viscometer | 26.3 cps | 19.7 cps | 19.7 cps |
| Lovibond Color | AOCS Method Cc 13b-45 | 8 Red/ 79 Yellow | 20 Red/ 77 Yellow | 16 Red/ 70 Yellow |
| Heat of Fusion | DSC | 121.6 mJ/mg | 99.4 mJ/mg | 86.9 mJ/mg | a capillary melting point of 35°–36° C. and a DSC melting point of 35. NMR in CDCl$_3$ (chemical shifts in ppm): 5.25 (m, 1H), 4.3 (dd, 2H), 4.15 (dd, 2H), 2.3 (m, 2H), 2.1 (m, 6H), 1.6 (m, 2H), 1.3 (m, 28H), 0.9 (t, 3H).

Dipropionyl monostearin is prepared by melting 771 g (2.15 moles) 1-glycerol-rac-monostearin obtained from Spectrum Chemicals (Lot # FC026) in a 2-L reaction flask equipped with a magnetic stirrer, heating mantle, thermometer, and reflux condenser prior to adding 552 g (4.24 moles) propionic anhydride (Aldrich Chemicals). The reaction flask is heated to 167° C. for 8 hours at atmospheric pressure, and the side product removed by vacuum distillation at 65 mm Hg, 35° C. The golden yellow solf solid product is passed through a falling film still equipped with mesitylene as a boiling solvent (168° C., <1 mm Hg) and deodorized to afford 935.5 g (1.98 moles, 94%) of a golden yellow soft solid having a DSC melting point of 24° C. SFC analysis: 96.5% SPP/PSP, 3.3% SPS/SSP, 0.2% SSS, <<1% unreacted material. NMR in CDCl$_3$ (chemical shifts in ppm): 5.25 (m, 1H), 4.3 (dd, 2H), 4.15 (dd, 2H), 2.35 (m, 6H), 1.6 (m, 2H), 1.25 (m, 28H), 1.1 (m, 6H), 0.9 (t, 3H).

Dibutyryl monostearin is prepared by melting 864.2 g (2.47 moles) 1-glycerol-rac-monostearin obtained from Spectrum Chemicals (Lot # FC026) in a 2-L reaction flask equipped with a magnetic stirrer, heating mantle, thermometer, and reflux condenser prior to adding 770.4 g (4.87 moles) burytic anhydride (Aldrich Chemicals). The reaction flask is heated to 180° C. for 16 hours at atmospheric pressure, and the butyric acid side product is removed by vacuum distillation at 100 mm Hg, 105° C. The yield of distillate is quantitative. The milky golden liquid product is passed through a falling film still equipped with mesitylne as the boiling solvent (168° C., <1 mm Hg) and steam deodorized at 210° C., <1 mm Hg. The yield is 2.08 moles (86.8%) of a golden yellow very soft solid having a DSC melting point of 21° C. SFC analysis: 94.2% SBB/BSB, 5.3% SBB/BSB, 4% 1-monostearin. NMR in CDCl$_3$ (chemical shifts in ppm) indicates 95% product: 5.25 (m, 1H), 4.3 (dd, 2H), 4.15 (dd, 2H), 2.35 (m, 6H), 1.6 (m, 6H), 1.25 (m, 28H), 1.1 (m, 6H), 0.9 (t, 3H).

Dihexanyl monostearin is prepared by melting 775.5 g (4.32 moles) 1-glycerol-rac-monostearin obtained from Spectrum Chemicals (Lot # FC026) in a 2-L reaction flask equipped with a magnetic stirrer, boiling chips, heating mantle, thermometer, and reflux condenser prior to adding 775.5 g (2.16 moles) hexanoic anhydride (Aldrich Chemicals). The reaction flask is heated to 250° C. for 8 hours at atmospheric pressure, and the hexanoic acid side product is removed by vacuum distillation at >1 mm Hg, 70° C. The yield of distillate is quantitative. The product is passed through a falling film still equipped with mesitylne as the boiling solvent (168° C., <1 mm Hg) and steam deodorized at 210° C., <1 mm Hg. The yield is 2.12 moles (97.9%) of a golden yellow very soft solid having a DSC melting point of 13° C. NMR in CDCl$_3$ (chemical shifts in ppm) indicates 99% product: 5.25 (m, 1H), 4.3 (dd, 2H), 4.15 (dd, 2H), 2.3 (m, 6H), 1.6 (m, 6H), 1.25 (m, 36H), 0.9 (t, 3H).

Dioctanyl monostearin is prepared by melting 200 g (0.56 moles) 1-glycerol-rac-monostearin obtained from Spectrum Chemicals (Lot # FC026) in a 1-L reaction flask equipped with a magnetic stirrer, boiling chips, heating mantle, thermometer, and reflux condenser prior to adding 316.7 g (1.17 moles) octanoic anhydride (American Tokyo Kasei Inc). The reaction flask is heated to 250° C. for 10 hours at atmospheric pressure, and the octanoic acid side product is removed by vacuum distillation at 100 mm Hg, 160° C. The yield of distillate is quantitative. The product is passed through a falling film still equipped with mesitylne as the boiling solvent (168° C., <1 mm Hg) and then steam deodorized at 210° C., <1 mm Hg. The yield is 320.2 g (0.52 moles, 93.6%) of a brown solid having a capillary melting point of 38°–41° C. and a DSC melting point of 37° C. NMR in CDCl$_3$ (chemical shifts in ppm) indicate 97.8% product: 5.25 (m, 1H), 4.3 (dd, 2H), 4.15 (dd, 2 H), 2.3 (m, 6H), 1.6 (m, 6H), 1.25 (m, 36H), 0.9 (t, 9 H).

Dicapryl monostearin is prepared by melting 269 g (0.75 moles) 1-glycerol-rac-monostearin obtained from Spectrum Chemicals (Lot # FC026) in a 3-L reaction flask equipped with a magnetic stirrer, boiling chips, heating mantle, thermometer, and reflux condenser prior to adding 489.8 g (1.5 moles) decanoic (capric) anhydride (TCI Chemicals, lot FC 001). The reaction flask is heated to 200° C. for 10 hours at atmospheric pressure, and the capric acid side product is removed by vacuum distillation at 100 mm Hg, 160° C. The yield of distillate is quantitative. The brown soft solid product is passed through a falling film still equipped with mesitylne as the boiling solvent (168° C., <1 mm Hg) and then steam deodorized at 210° C., <1 mm Hg. The yield is 429.98 g (0.64 moles, 85.9%) of a golden yellow soft solid having a DSC melting point of 35.7° C. and a capillary melting point of 31°–33° C. NMR in CDCl$_3$ (chemical shifts in ppm) indicates 98% product: 5.25 (m, 1H), 4.3 (dd, 2H), 4.15 (dd, 2H), 2.3 (m, 6H), 1.6 (m, 6H), 1.25 (m, 36H), 0.9 (t, 9H).

Dilauryl monostearin is prepared by melting 11.65 g (0.03 moles) 1-glycerol-rac-monostearic obtained from Spectrum Chemicals (Lot # FC026) in a 200-mL reaction flask equipped with a magnetic stirrer, boiling chips, heating mantle, thermometer, and reflux condenser prior to adding 25 g (0.065 moles) lauric anhydride (TCI Chemicals). The reaction flask is heated to 200° C. for 10 hours at atmospheric pressure, and the capric acid side product is removed by vacuum distillation at <5 mm Hg, 180° C. The yield of distillate is quantitative. The product is passed through a falling film still equipped with mesitylne as the boiling solvent (168° C., <1 mm Hg) and then steam deodorized at 210° C., <1 mm Hg. The yield is 20.1 g (0.58 moles, 4.9%) of a golden yellow solid having a DSC melting point of 38.7° C. and a capillary melting point of 33°–36° C. NMR in CDCl$_3$ (chemical shifts in ppm) indicates 98% product: 5.25 (m, 1H), 4.3 (dd, 2H), 4.15 (dd, 2H), 2.3 (m, 6H), 1.6 (m, 6H), 1.25 (m, 36H), 0.9 (t, 9H).

The data show a progressive decrease in melting point from 73° C. for the beta form of tristearin to 38.7° C. for dilauryl monostearin to 35°–36° for didecanyl monostearin to 13° C. for dihexanyl monostearin. This result can be correlated with generally expected decreases in melting points with decreasing sizes of the molecules. However, as the chain length is further decreased, the melting point surprisingly rises: 21° for dibutyryl monostearin, 24° C. for dipropionyl monostearin, and 38° C. for diacetyl monostearin.

The low melting behavior of the dihexanyl derivative is in agreement with previously reported data wherein the $C_6$ triglycerides were found to have minimum melting points in the $C_{18}C_nC_{18}$ and $C_nC_nC_{18}$ series, n=2 to 18 (Jackson, et al., and Jackson and Lutton, cited above).

Example 39

This example compares and contrasts-cocoa butter with various low calorie triglycerides in chocolate coating compositions. The DSC melting profile of tempered cocoa butter control (-▷-), which hardens into a slightly waxy form after several months (···◆···), is compared with quench cooled cocoa butter (-⊖-) in FIG. 1.

The coatings are prepared by mixing equal parts confectioner's sugar, cocoa powder, and test fat thoroughly at 55° to 65° C. with 0.5% by weight lecithin. The mixture is then poured into molds and allowed to cool to ambient temperature or refrigerated.

Figure 2:
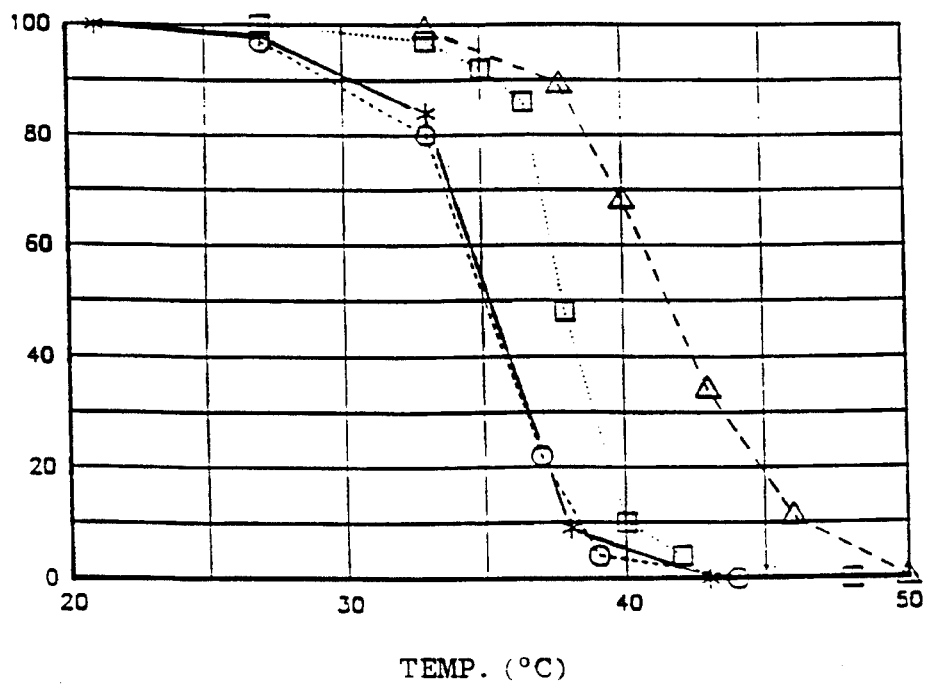
FIG. 2 shows DSC solid fat indices of chocolate coating compositions containing a low calorie triglyceride mixture obtained by interesterifying 4.5 moles triacetin with 1 mole hydrogenated canola and then steam deodorizing, run at zero time (–⊖–), after 11 days (····•····), and after 17 days (–+–) at ambient temperature, compared with a control coating composition containing tempered cocoa butter (- ▷ -).

A triglyceride mixture is prepared by the interesterification of 4.5 moles triacetin with 1.0 mole hydrogenated canola as outlined in Example 20. The resulting mixture was determined by SFC to contain 70% SSL/SLS, 27% SLL/LSL, and 3% LLL. A chocolate coating prepared with this fat had a DSC melting profile (-⊖-) and mouthfeel similar to a coating prepared with cocoa butter (-▷-) on the first day, but hardened over time as illustrated in FIG. 2 (11 days, (···◆···); 17 days, (-✱-). The coating had the mouthfeel of candlewax after only a few days at room temperature.

Diacetostearin was prepared by the direct esterification of 97% glycerol monostearate with acetic anhydride as outlined in Example 3. The resulting mixture was determined by SFC to contain less than 5% SLL/LSL and LLL. A chocolate coating prepared with this fat had a melting profile and mouthfeel similar to a coating made with cocoa butter. The test coating hardened very slowly over a period of a year to a slightly waxy form. No bloom was noticeable after 18 months at room temperature, and the flavor did not change compared to a control held in the freezer in a sealed container.

Figure 3:
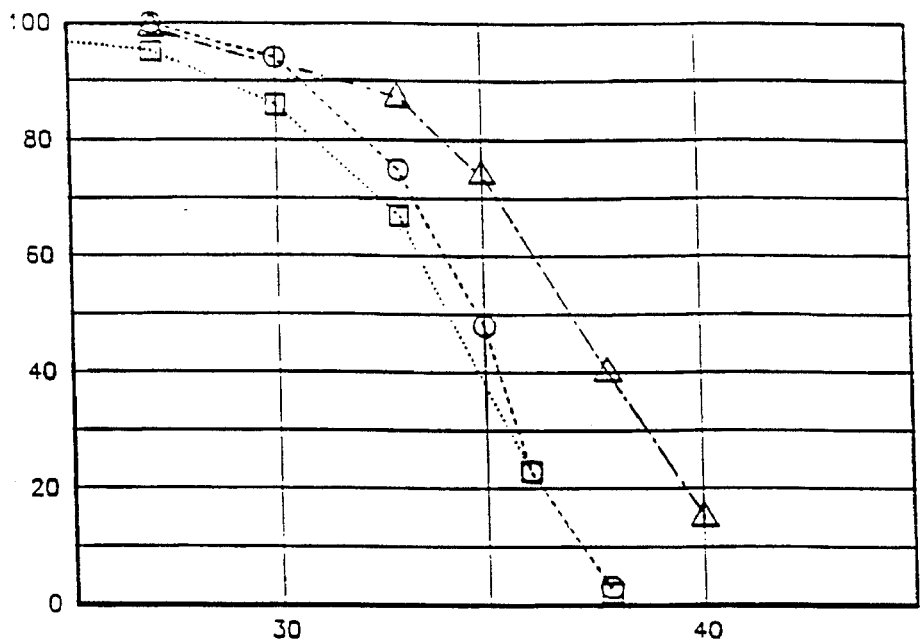
FIG. 3 shows DSC solid fat indices of chocolate coating compositions containing a low calorie triglyceride mixture obtained by interesterifying triacetin, tripropionin, and hydrogenated canola in a reactant molar ratio of 2.5:2:1 and then steam deodorizing, run at zero time (····•····) and after 2 days at 25° C. (–✻–), compared with a control coating composition containing tempered cocoa butter (–⊖–).

Hydrogenated canola was interesterified with triacetin and tripropionin as described in Example 24 in a ratio of 1:2:2.5. The resulting mixture was determined by SFC to contain 71% SSL/SLS, 27% SLL/LSL, and 2% LLL. As depicted in FIG. 3, a chocolate coating prepared with this fat had a DSC melting profile (···◆···) similar to a coating made with cocoa butter (-⊖-). The test coating stabilized to a slightly higher melting form after two days (-✱-), which persisted over the course of the study. The mouthfeel was acceptable, but the coating was soft. In addition, after 20 days at 75° F., a whitish bloom appeared that grew worse as time passed. The bloom was scraped from the surface, subjected to DSC and SFC analysis, and found to contain mostly SLL/LSL species.

Figure 4:
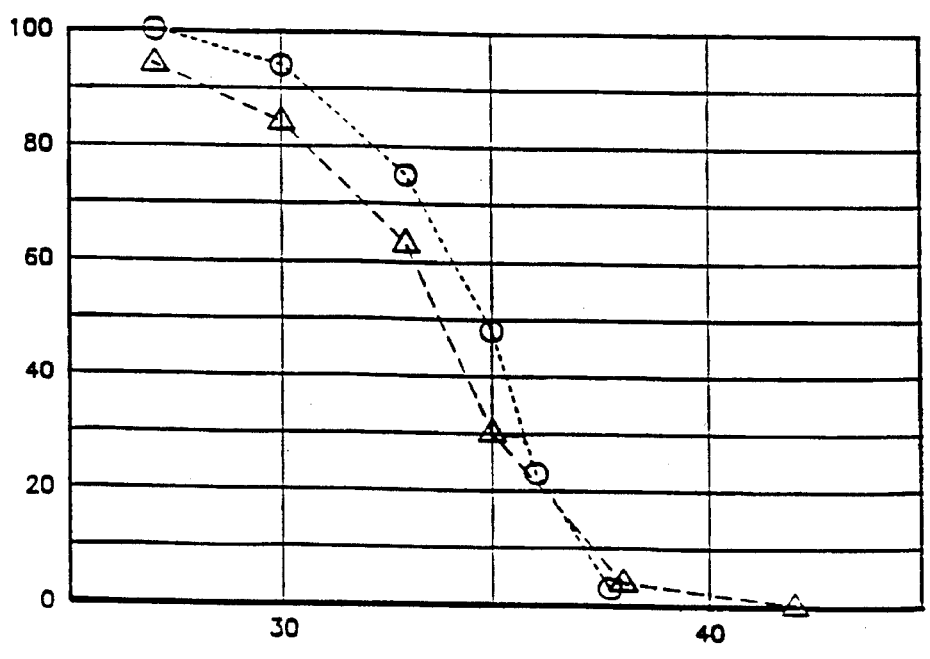
FIG. 4 shows DSC solid fat indices of chocolate coating compositions containing a low calorie triglyceride mixture obtained by interesterifying triacetin, tripropionin, and hydrogenated canola in a reactant molar ratio of 11:1:1 and then steam deodorizing (—*—) compared with a control coating composition containing tempered cocoa butter (—◯—); the melting profile of the low calorie mixture retains a lower than cocoa butter profile for at least 3 months when stored at either 65° F. or 75° F.

A desirable low calorie triglyceride mixture was prepared by interesterifying 11 moles triacetin and 1 mole tripropionin with hydrogenated canola as outlined in Example 36. The resulting mixture was determined by SFC to contain 85% SSL/SLS, 14.5% SLL/LSL, and 0.5% LLL. FIG. 4 shows that a coating prepared from this mixture (-✱-) is lightly softer, but similar to a coating prepared with cocoa butter (-⊖-). The coating hardens somewhat over time, but didn't become waxy; it has a lower DSC melting profile than cocoa butter after a 3-month storage at either 75° F. or 65° F. No trace of bloom was observed in samples stored at 75° F. after 3 months, and the odor and flavor remained very good.

Example 40

This example compares and contrasts cookies having a shortening component formulated with low calorie triglycerides of this invention and control cookies formulated with an all purpose vegetable shortening (Centrasoy™).

Reduced calorie fat mixtures are prepared as described in Examples 24 and 36 using interesterification mixtures containing the following different reactant molar ratios of hydrogenated canola:tripropionin:triacetin and analyzed using SFC to determine the SSL/SLS, SLL/LSL, and LLL components as described in Example 21:

| Mixture | SSL/SLS | SLL/LSL | LLL |
|---|---|---|---|
| Mixture B from 1:1:11 | 82.8 | 16.1 | 1.1 |
| Mixture C from 1:11:1 | 84.8 | 14.41 | 0.8 |
| Mixture D from 1:3:9 | 87.9 | 11.6 | 0.5 |
| Mixture E from 1:6:6 | 84.4 | 13.8 | 1.8 |
| Mixture F from 1:9:3 | 88.0 | 11.4 | 0.7 |

Figure 5:
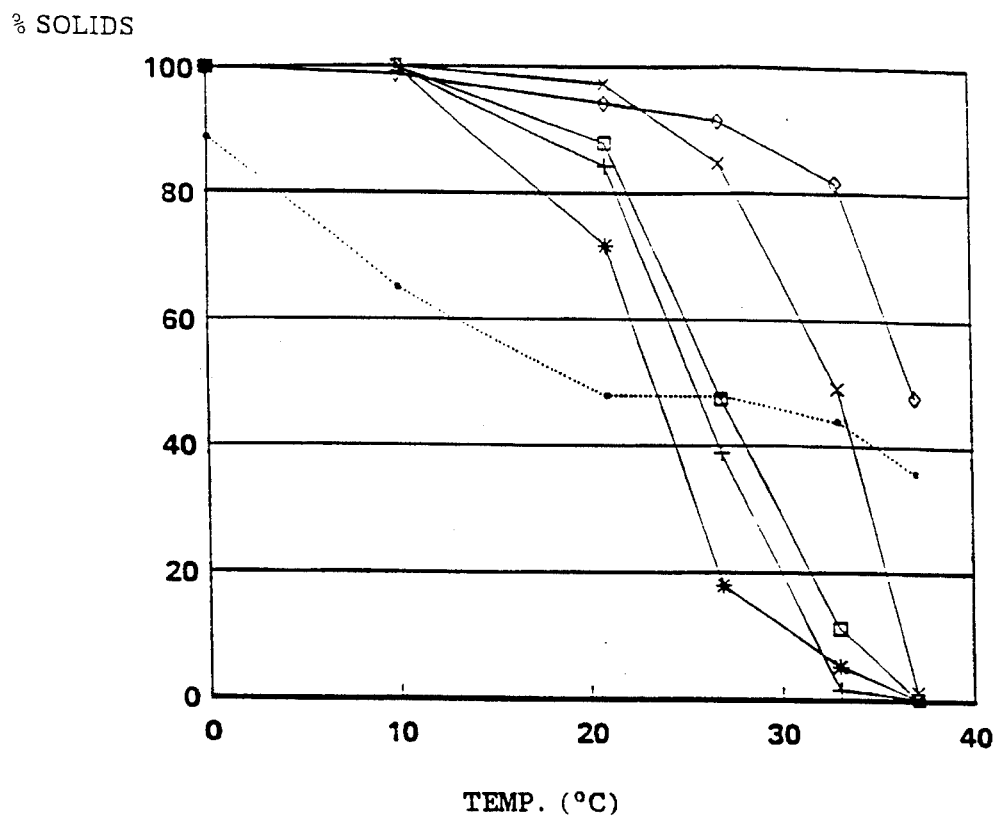
FIG. 5 shows DSC solid fat indices of six triglyceride compositions: an all purpose vegetable shortening control (—▫—) and five low calorie triglyceride mixtures obtained by interesterifying and steam deodorizing triacetin, tripropionin, and hydrogenated canola in a reactant molar ratio of 1:11:1 , (—*—), 3:9:1 (—◯—), 6:6:1 (—◆—), 9:3:1 (—△—), and 11:1:1 (———).

The solid fat index for each mixture is measured using DSC. The area under the melting peak curves are integrated to give percent liquid at the desired temperatures of 0° C., 10° C., 21.1° C., 26.7° C., 33.3° C., and 37.8° C. These values are then converted to percent solids. Using this methodology, the data are obtained are plotted in FIG. 5, with the control depicted as -⊟- mixture B as -●-, mixture C as -◁-, mixture D as -△-, mixture E as -◆- and mixture F as -▷-. It can be seen that at room temperature, mixtures C and F are closest to the control shortening value of about 50% solids.

| | | grams |
|---|---|---|
| To prepare the cookies, mix | | |
| | fine granulated sugar | 72.0 |
| | brownulated brown sugar | 22.5 |
| | nonfat dry milk | 2.3 |
| | salt | 2.8 |
| | sodium bicarbonate | 2.3 |
| and then add | | |
| | control or test shortening | 90.0. |
| Add | high fructose corn syrup | 3.4 |
| then | ammonium bicarbonate | 1.1 |
| and | vanilla extract | 0.34 |
| to | water | calculated* |
| and add the water mixture to the shortening mixture. | | |
| Add | flour | calculated* |

*g flour = {(100–13% moisture basis)/(100-flour moisture %)}
*225 g water = 225 g − g flour added + 49.5

Sheet and cut the dough according to AACC Method 10-22. Bake at 400° F. for 10 minutes in a National reel test bake oven.

*g flour={(100–13% moisture basis)/(100-flour moisture %)}*225 g g water= 225 g−g flour added+49.5

Dough viscosity is measured using a Stevens-LFRA™ texture analyzer. Immediately after preparing the dough, 109 grams are added to the LFRA cup and compressed to a constant volume. A spherical probe is then plunged into the dough 15 mm at a rate of 2 mm/sec. Five measurements are taken for each dough and the average load value (grams) is reported. Using this method, cookie dough made using the control shortening had a LFRA value of 112; using mixture B, 1105; using mixture C, 180; using mixture D, 717; using mixture E, 296; and using mixture F, 136. Desirable processability LFRA values fall between about 100 and about 300, so that mixtures C, E, and F are acceptable shortenings in this cookie recipe, but mixtures B and D (high in acetic acid residues) make the dough too stiff.

During baking, the dough blank weights and cookie weights are measured and recorded. The following equation is then used to calculate the percent weight loss during baking:

$$\text{weight loss} = 100 * (dbw - cw)/dbw$$

where dbw=dough blank weight and cw=cookie weight. Final cookie moisture measurements are made using a Computrac™ set at 150° C. Three runs of each sample are tested and an average moisture in % is recorded. Using this methodology, the following data are obtained:

| sample | weight loss | moisture |
|---|---|---|
| control | 12.32 | 5.65 |
| B | 9.27 | 7.59 |
| C | 8.60 | 8.56 |
| D | 10.51 | 10.60 |
| E | 9.34 | 7.68 |
| F | 6.60 | 9.62 |

All the test compounds have higher moisture, i.e., lower weight loss during baking, than the control.

After baking, the cookies are measured. Using a micrometer, the cookie diameter/spread (mm) are measured on at least 3 cookies in 4 locations. An average value is obtained and reported as an average cookie diameter. Four cookies are then stacked and the stack height is measured. Average cookie height is then obtained by dividing by the number of cookies. Using these measurements the following data are obtained:

| sample | diameter (mm) | height (mm) |
|---|---|---|
| control | 82.65 | 9.22 |
| B | 80.09 | 15.52 |
| C | 70.84 | 11.76 |
| D | 73.40 | 14.44 |
| E | 71.23 | 13.59 |
| F | 71.46 | 10.17 |

All the test shortenings have smaller diameters, but higher stack heights, than the control. Among the materials tested, those with more propionic acid residues exhibited somewhat less spread and those with less propionic acid residues achieved greater height.

Product color is evaluated using a Minolta Chroma™ meter model CR-210 to measure L, a rating of light to dark (<~30 is dark); a, a sense of intensity of hue and a measure of red-green; and b, a sense of intensity of chroma and a measure of yellow-blue (roughly comparable to Hunter L, a, and b values). Desirable cookies exhibit red a values and yellow b values. Three cookies are measured three times and averaged for both top and bottom colors. Using this technique, the following data are obtained:

| sample | TOP: L,a,b | BOTTOM: L,a,b |
|---|---|---|
| control | 65.09, 6.11, 33.17 | 45.46, 14.93, 29.44 |
| B | 63.45, 7.03, 31.49 | 42.78, 16.63, 30.70 |
| C | 62.44, 6.75, 30.68 | 45.41, 15.11, 31.71 |
| D | 63.60, 6.10, 30.30 | 43.10, 15.98, 31.11 |
| E | 56.80, 9.29, 30.11 | 39.76, 15.98, 28.94 |
| F | 61.78, 6.54, 31.08 | 45.66, 15.82, 30.96 |

With the exception of sample E, which produced a darker cookie, there are no significant differences in any of the color values.

Texture of the baked cookies is evaluated using an Instron™ 4501 Universal Testing machine, which punctures the cookies and measures resistance to a small probe.

Values for stress and moduli, which can be correlated with hardness, fracturability and/or brittleness, are calculated based on the resistant force versus distance. Using this technique, the following data are obtained:

| sample | stress (kg/mm$^2$) | moduli (kg/mm$^2$) |
|---|---|---|
| control | 0.435 | 8.07 |
| B | 0.638 | 17.17 |
| C | 0.293 | 9.20 |
| D | 0.115 | 3.15 |
| E | 0.168 | 6.31 |
| F | 0.154 | 4.69 |

The varying degrees of stress and moduli obtained suggest that textural attributes from cake-like to a dense snap cookie can be achieved.

Example 41

Like Example 40 above, this example evaluates cookies having a shortening component formulated with low calorie triglycerides of this invention, except that the triglycerides are blends rather than interesterified mixtures.

Low calorie chocolate chips are first prepared. Diacetyl stearin, 150 g, is melted and blended with 150 g cocoa powder, 150 g confectioner's sugar and 4.5 g lecithin, deposited into nibs and processed into chips.

A blend of 35% diacetyl stearin and 65% dipropionyl stearin, which had a broad DSC melting range between about −15° and 40° C., is employed in the cookie recipe of Example 40 and compared with an all purpose vegetable shortening control cookie. Before baking, 112.5 grams chocolate chips formulated as described above are mixed into the test dough; Wilbur's real chocolate chips are used in the control. The cookies are baked at 420° for 10 minutes.

Figure 6:
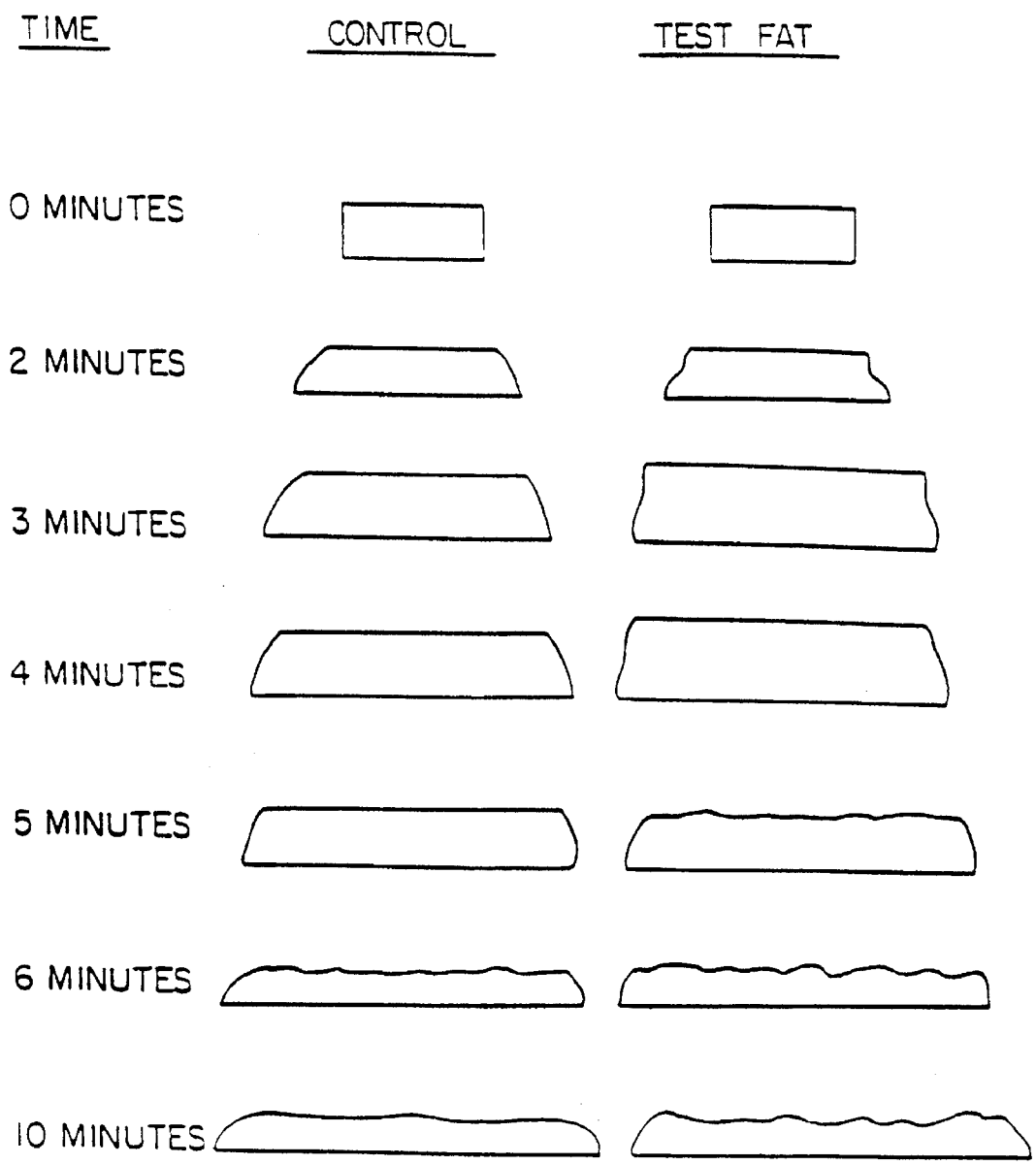
FIG. 6 shows a pictorial comparison of cross-sectional geometrical changes that occur during the baking of otherwise identical cookies containing an all purpose vegetable shortening control (left) and a low calorie triglyceride test mixture containing 35% diacetyl stearin and 65% dipropionyl stearin (right).

The baking behavior is depicted in FIG. 6, which compares the control cookie with the low calorie dipropionyl stearin/diacetyl stearin shortening cookie. At the two minute mark, the low calorie dough blank started to spread in an unusual steplike pattern. The cookies achieved a fairly high rise at 3 minutes and did not start to spread out until almost 4 minutes into the bake. Collapse occurred around the 5 minute mark and setting and browning began to occur at 6 minutes. The final cookie had a nice brown color with low spread and high stack height. Color analysis using the Minolta Chroma™ meter described in the previous Example gave an L value of 59.56, an a value of 8.04 and a b value of 34.1. The diacetyl stearin chocolate chips stood up well under baking.

Figure 7:
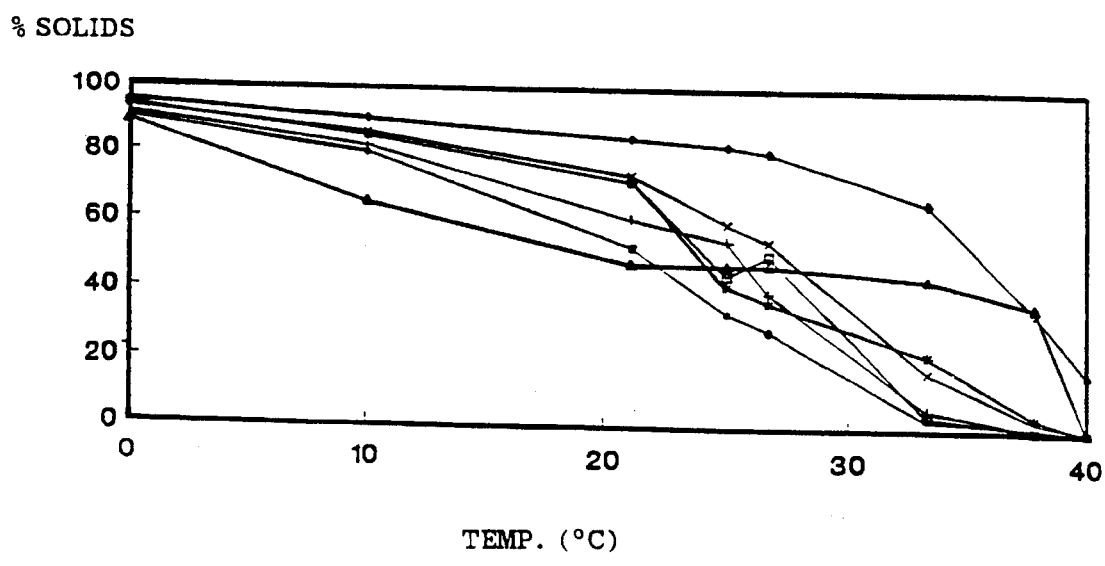
FIG. 7 shows DSC solid fat indices of seven triglyceride compositions: an all purpose vegetable shortening control (———), a 1:2 blend of diacetyl stearin and dibutyryl stearin (—*—), a 1:1 blend of diacetyl stearin and dibutyryl stearin (—▫—), a 2:1 blend of diacetyl stearin and dibutyryl stearin (—◁—), a 1:2 blend of diacetyl stearin and dipropionyl stearin (—◆—), a 1:1 blend of diacetyl stearin and dipropionyl stearin (—△—), and a 4:1 blend of diacetyl stearin and dipropionyl stearin (———).

The experiment is repeated comparing control cookies with cookies having shortening components comprising diacetyl stearin and either dibutyrl stearin or dipropionyl stearin. FIG. 7 shows DSC solid fat indices of different blends of diacetyl stearin with dipropionyl or dibutyryl stearin compared with a vegetable oil shortening control ( ─┼─ ). In the figure, -◇- is a 1:1, ··□·· is a 1:2 and -▷- is a 2:1 blend of diacetyl stearin and dibutyryl stearin; -△- is a 1:1, and ──, a 4:1 blend of diacetyl stearin and dipropionyl stearin.

Using the same control cookies containing an all purpose vegetable shortening and real Wilbur's chocolate chips, cookies formulated with a shortening comprising diacetyl stearin and dibutyryl stearin blended in equal proportions and diacetyl stearin chocolate chips (recipe G), and cookies formulated with a shortening comprising diacetyl stearin and dipropionyl stearin blended in equal proportions and diacetyl stearin chocolate chips (recipe H) are prepared and baked.

Geometric and color measurements using the methodology of the above Example yielded the following data:

| recipe | stack height (mm) | width (mm) | color (L,a,b) |
|---|---|---|---|
| control | 1.125 | 8.1 | 56.51, 6.99, 27.81 |
| G | 1.250 | 7.0 | 51.97, 10.84, 29.82 |
| H | 1.125 | 7.5 | 57.43, 8.23, 30.24 |

The control cookies came out flat and pale. The recipe G cookies required 11 minutes to bake (instead of 10) and came out dark and mottled, with high stack height and little spread. The recipe H cookies had good stack height, good spread and good color.

Example 42

Cookies.
Another cookie batch is prepared by mixing

| Ingredient | | grams |
|---|---|---|
| | Granulated Sugar | 12.8 |
| | Brownulated Brown Sugar | 4.0 |
| | Nonfat Dry Milk | 0.4 |
| | Salt | 0.5 |
| | Sodium Bicarbonate | 0.4 |
| | A Dibutylstearin (35%) and Corn Oil (65%) Blend | 16.0 |
| To this is added | | |
| | Water | 8.8 |
| | High Fructose Corn Syrup | 0.6 |
| | Ammonium Bicarbonate | 0.2 |
| Then | Flour | 40.0 |

The dough is sheeted, cut and baked in the usual manner.

Example 43

Ice Cream.
Chocolate ice cream is prepared by mixing

| Ingredient | parts |
|---|---|
| Water | 60.6 |
| Example 37 Triglyceride Mixture B | 10.0 |
| Nonfat Dry Milk | 10.0 |
| Sugar | 10.0 |
| Corn Syrum | 6.0 |
| Dricol ™ Texture Enhancer | 0.3 |
| Cocoa Light | 3.0 |
| Lecithin | 0.1 |

The ingredients are heated to pasturize, then cooled slightly, homogenized, and pumped into a heat exhanger whereupon the temperature is rapidly reduced. After the initiation of fat crystallization, the mixture is frozen.

Example 44

Cream Filling.
To make a cream filling, combine

| Ingredient | | grams |
|---|---|---|
| | Sugar (6x) | 376 |
| with | Example 2 Diacetyl Stearin | 160 |
| | Example 14 Dipropionyl Stearin | 24 |
| | Example 36 Dihexanyl Stearin | 14 |
| | Lecithin | 2 |
| and | Vanilla | 0.3 |

The filling had a smooth texture and mouthfeel and a solids content of 90% at 50° F., 78% at 70° F., 60% at 80° F., 15% at 92° F., and 0% at 100° F., which remained stable a week at room temperature.

Example 45

Sandwich Cookies.
Basecakes may be prepared by combining parts

| | parts |
|---|---|
| Flour | 48.0 |
| High Fructose Corn Syrup | 12.0 |
| Sugar (6x) | 10.0 |
| Example 24 1:2.5:2.5 Triglyceride Mixture | 10.0 |
| Dutched Cocoa | 5.0 |
| Corn Syrup (42 D.E.) | 3.0 |
| Dextrose | 2.0 |
| Frozen Whole Eggs | 2.0 |
| Salt | 0.3 |
| Sodium Bicarbonate | 0.2 |
| Lecithin | 0.2 |
| Vanilla | 0.2 |
| Ammonium Bicarbonate | 0.1 |
| Water | 7.0 | mixing well, rotary molding, baking and cooling. Sandwich cookies are prepared by filling the basecakes with the filler of previous Example 44 in a weight ratio of 100 parts basecake to 40.5 parts filler.

The cookies may, optionally, be enrobed with a coating prepared by blending 150 g melted diacetyl stearin, 150 g dutched cocoa powder, 150 g confectioner's sugar and 4.5 g lecithin.

Example 46

Shortening.
A shortening may be prepared by interesterifying 2 moles of tributyrin with 1 mole of hydrogenated canola as outlined in Example 20.

Example 47

Margarine.
A stick margarine may be prepared by emulsifying

| | parts |
|---|---|
| Oil Phase Ingredients | |
| Example 20 1:2.5 Triglyceride Mixture | 40 |
| Liquid Corn Oil | 40 |
| Lecithin | 0.3 |
| Mono- and Di-glycerides | 0.21 |
| Margarine Flavor and Color | 0.0062 |
| with Aqueous Phase Ingredients | |
| Water | 16.4 |
| Whey | 1.00 |
| Salt | 2.00 |
| Sodium Benzoate | 0.086 | and passing the emulsion through a cooled, scraped-surface heat exchanger in the usual process.

Example 48

Low Fat Spread.
A 60% table spread may be prepared by emulsifying

| | parts |
|---|---|
| Oil Phase Ingredients | |
| A 65:35 Blend of Corn Oil: Example 20 1:1.25 Triglycerides | 59.58 |
| Lecithin | 0.20 |
| Distilled Monoglycerides from Unhydrogenated Sunflower Oil | 0.20 |
| Beta-carotene and Vitamin A Palmitate in Corn Oil | 0.005 |
| Flavor | 0.010 |
| ith Aqueous Phase Ingredients | |
| Water | 37.86 |
| Salt | 2.00 |
| Potassium Sorbate | 0.10 |
| Phosphoric Acid | 0.04 | and passing the emulsion through a cooled, scraped-surface heat exchanger in the usual process.

Example 49

Low Fat Spread.
A 40% table spread may be prepared by emulsifying

| | parts |
|---|---|
| Oil Phase Ingredients | |
| A 75:25 Blend of Corn Oil: Example 14 Triglycerides | 39.38 |
| Lecithin | 0.10 |
| Distilled Monoglycerides from Unhydrogenated Sunflower Oil | 0.50 |
| Flavor | 0.010 |
| with Aqueous Phase Ingredients | |
| Water | 57.86 |
| Salt | 2.00 |
| Potassium Sorbate | 0.10 |
| Calcium Disodium EDTA | 0.006 | and passing the emulsion through a cooled, scraped-surface heat exchanger in the usual process.

Example 50

Spray Oil.
A spray oil may be prepared by interesterifying 12 moles tributyrin with 1 mole of hydrogehated canola as outlined in Example 20.

Example 51

Low calorie triglycerides of this invention bearing two short residues and one long, saturated moiety include the following example compounds:

1-acetyl-3-palmitoyl-2-propionyl glyceride
2-acetyl-1-palmitoyl-3-propionyl glyceride
2-acetyl-1-propionyl-3-stearoyl glyceride
1-acetyl-2-propionyl-3-stearoyl glyceride
1-acetyl-3-arachidoyl-2-propionyl glyceride
2-acetyl-1-arachidoyl-3-propionyl glyceride
1-acetyl-3-behenoyl-2-propionyl glyceride
2-acetyl-1-behenoyl-3-propionyl glyceride
1-acetyl-2-butyryl-3-palmitoyl glyceride
2-acetyl-1-butyryl-3-palmitoyl glyceride
2-acetyl-1-butyryl-3-stearoyl glyceride
1-acetyl-2-butyryl-3-stearoyl glyceride
1-acetyl-3-arachidoyl-2-butyryl glyceride
2-acetyl-1-arachidoyl-3-butyryl glyceride
1-acetyl-3-behenoyl-2-butyryl glyceride
2-acetyl-1-behenoyl-3-butyryl glyceride
1-acetyl-3-palmitoyl-2-valeryl glyceride
2-acetyl-1-palmitoyl-3-valeryl glyceride
2-acetyl-1-stearoyl-3-valeryl glyceride
1-acetyl-3-stearoyl-2-valeryl glyceride
1-acetyl-3-arachidoyl-2-valeryl glyceride
2-acetyl-1-arachidoyl-3-valeryl glyceride
1-acetyl-3-behenoyl-2-valeryl glyceride
2-acetyl-1-behenoyl-3-valeryl glyceride
1-butyryl-3-palmitoyl-2-propionyl glyceride
2-butyryl-1-palmitoyl-3-propionyl glyceride
2-butyryl-1-propionyl-3-stearoyl glyceride
1-butyryl-3-stearoyl-2-propionyl glyceride
1-arachidoyl-2-butyryl-3-propionyl glyceride
1-arachidoyl-3-butyryl-2-propionyl glyceride
1-behenoyl-3-butyryl-2-propionyl glyceride
1-behenoyl-2-butyryl-3-propionyl glyceride
1-palmitoyl-2-propionyl-3-valeryl glyceride
1-palmitoyl-3-propionyl-2-valeryl glyceride
2-propionyl-1-stearoyl-3-valeryl glyceride
1-propionyl-3-stearoyl-2-valeryl glyceride
1-arachidoyl-2-propionyl-3-valeryl glyceride
1-arachidoyl-3-propionyl-2-valeryl glyceride
1-behenoyl-2-propionyl-3-valeryl glyceride
1-behenoyl-3-propionyl-2-valeryl glyceride
1-acetyl-2-palmitoyl-3-propionyl glyceride
1-acetyl-3-propionyl-2-stearoyl glyceride
1-acetyl-2-arachidoyl-3-propionyl glyceride
1-acetyl-2-behenoyl-3-propionyl glyceride
1-acetyl-3-butyryl-2-palmitoyl glyceride
1-acetyl-3-butyryl-2-stearoyl glyceride
1-acetyl-2-arachidoyl-3-butyryl glyceride
1-acetyl-2-behenoyl-3-butyryl glyceride
1-acetyl-2-palmitoyl-3-valeryl glyceride
1-acetyl-2-stearoyl-3-valeryl glyceride
1-acetyl-2-arachidoyl-3-valeryl glyceride
1-acetyl-2-behenoyl-3-valeryl glyceride
1-butyryl-2-palmitoyl-3-propionyl glyceride
1-butyryl-2-stearoyl-3-propionyl glyceride
2-arachidoyl-1-butyryl-3-propionyl glyceride
2-behenoyl-1-butyryl-3-propionyl glyceride
2-palmitoyl-1-propionyl-3-valeryl glyceride
1-propionyl-2-stearoyl-3-valeryl glyceride
2-arachidoyl-1-propionyl-3-valeryl glyceride
2-behenoyl-1-propionyl-3-valeryl glyceride Low calorie triglyceride mixtures of this invention can also include the following example compounds:

SSL Derivatives 1,2-diacetyl-3-palmitoyl glyceride
1,2-diacetyl-3-stearoyl glyceride
1,2-diacetyl-3-arachidoyl glyceride
1,2-diacetyl-3-behenoyl glyceride
1-palmitoyl-2,3-dipropionyl glyceride
1,2-dipropionyl-3-stearoyl glyceride
1-arachidoyl-2,3-dipropionyl glyceride 1-behenoyl-2,3-dipropionyl glyceride
1,2-dibutyryl-3-palmitoyl glyceride
1,2-dibutyryl-3-stearoyl glyceride
1-arachidoyl-2,3-dibutyryl glyceride
1-behenoyl-2,3-dibutyryl glyceride SLS Derivatives 1,3-diacetyl-2-palmitoyl glyceride
1,3-diacetyl-2-stearoyl glyceride
1,3-diacetyl-2-arachidoyl glyceride
1,3-diacetyl-2-behenoyl glyceride
2-palmitoyl-1,3-dipropionyl glyceride
1,3-dipropionyl-2-stearoyl glyceride
2-arachidoyl-1,3-dipropionyl glyceride
2-behenoyl-1,3-dipropionyl glyceride
1,3-dibutyryl-2-palmitoyl glyceride
1,3-dibutyryl-2-stearoyl glyceride
2-arachidoyl-1,3-dibutyryl glyceride
2-behenoyl-1,3-dibutyryl glyceride LLS Derivatives 1-acetyl-2,3-dipalmitoyl glyceride
1-acetyl-2,3-distearoyl glyceride
1-acetyl-2,3-diarachidoyl glyceride
1-acetyl-2,3-dilignoceroyl glyceride
1-acetyl-2,3-dibehenoyl glyceride
1,2-dipalmitoyl-3-propionyl glyceride
1-propionyl-2,3-distearoyl glyceride
1,2-diarachidoyl-3-propionyl glyceride
2-propionyl-1,3-distearoyl glyceride
1,2-dibehenoyl-3-propionyl glyceride
1,2-diarachidoyl-3-butyryl glyceride
1-butyryl-2,3-dipalmitoyl glyceride
1-butyryl-2,3-dicerotoyl glyceride
1-acetyl-2-palmitoyl-3-stearoyl glyceride
1-acetyl-3-palmitoyl-2-stearoyl glyceride
1-acetyl-3-arachidoyl-2-palmitoyl glyceride
1-acetyl-2-arachidoyl-3-palmitoyl glyceride
1-acetyl-3-behenoyl-2-palmitoyl glyceride
1-acetyl-2-behenoyl-3-palmitoyl glyceride
1-acetyl-2-arachidoyl-3-stearoyl glyceride
1-acetyl-3-behenoyl-2-stearoyl glyceride
1-acetyl-3-arachidoyl-2-stearoyl glyceride
1-acetyl-2-behenoyl-3-stearoyl glyceride
1-acetyl-2-arachidoyl-3-behenoyl glyceride
1-acetyl-3-arachidoyl-2-behenoyl glyceride
1-palmitoyl-3-propionyl-2-stearoyl glyceride
1-palmitoyl-1-propionyl-3-stearoyl glyceride
1-arachidoyl-2-palmitoyl-3-propionyl glyceride
1-behenoyl-2-palmitoyl-3-propionyl glyceride
2-arachidoyl-1-palmitoyl-3-propionyl glyceride
2-behenoyl-1-palmitoyl-3-propionyl glyceride
1-arachidoyl-3-propionyl-2-stearoyl glyceride
1-behenoyl-3-propionyl-2-stearoyl glyceride
2-arachidoyl-1-propionyl-3-stearoyl glyceride
2-behenoyl-1-propionyl-3-stearoyl glyceride
1-butyryl-2-palmitoyl-3-stearoyl glyceride
2-arachidoyl-1-butyryl-3-palmitoyl glyceride
1-butyryl-3-palmitoyl-2-stearoyl glyceride
1-arachidoyl-3-butyryl-2-palmitoyl glyceride
2-behenoyl-1-butyryl-3-palmitoyl glyceride
1-behenoyl-3-butyryl-2-palmitoyl glyceride
1-arachidoyl-3-butyryl-2-stearoyl glyceride
2-arachidoyl-1-butyryl-3-stearoyl glyceride
2-behenoyl-1-butyryl-3-stearoyl glyceride
1-behenoyl-3-butyryl-2-stearoyl glyceride
1-arachidoyl-2-behenoyl-3-butyryl glyceride
2-arachidoyl-1-behenoyl-3-butyryl glyceride LSL Derivatives 2-acetyl-1,3-dipalmitoyl glyceride
2-acetyl-1,3-distearoyl glyceride
2-acetyl-1,3-diarachidoyl glyceride
2-acetyl-1,3-dibehenoyl glyceride
1,3-diarachidoyl-2-propionyl glyceride
1,3-dibehenoyl-2-propionyl glyceride
2-butyryl-1,3-dipalmitoyl glyceride
1,3-dipalmitoyl-2-propionyl glyceride
1,3-diarachidoyl-2-butyryl glyceride
1,3-dibehenoyl-2-butyryl glyceride
2-acetyl-1-palmitoyl-3-stearoyl glyceride
2-acetyl-1-behenoyl-3-palmitoyl glyceride
2-acetyl-1-arachidoyl-3-palmitoyl glyceride
2-acetyl-1-arachidoyl-3-stearoyl glyceride 2-acetyl-1-behenoyl-3-stearoyl glyceride
1-palmitoyl-2-propionyl-3-stearoyl glyceride
1-arachidoyl-3-palmitoyl-2-propionyl glyceride
1-behenoyl-3-palmitoyl-2-propionyl glyceride
1-behenoyl-2-propionyl-3-stearoyl glyceride
1-arachidoyl-3-behenoyl-2-propionyl glyceride
2-butyryl-1-palmitoyl-3-stearoyl glyceride
1-arachidoyl-2-butyryl-3-palmitoyl glyceride
1-behenoyl-2-butyryl-3-palmitoyl glyceride
1-arachidoyl-2-butyryl-3-stearoyl glyceride
1-behenoyl-2-butyryl-3-stearoyl glyceride
1-arachidogyl-3-behenoyl-2-butyryl glyceride The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. A chocolate composition containing a sweetener, a chocolate flavor, and a fat component, the fat component comprising at least 25 weight % of a mixture of at least two triglycerides of the following formulae

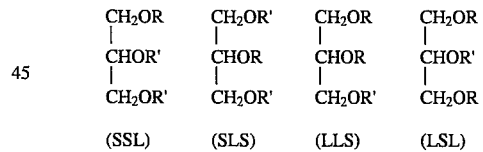

wherein
  each R, independently, is a long chain saturated fatty acid residues having between 16 and 22 carbons; and
  each R' is a short chain acid residue derived from propionic acid,
and the mixture contains greater than about 25% LLS and LSL species and the fat component exhibits a melting profile similar to cocoa butter.

2. A composition according to claim 1 wherein at least about 70% of the R groups are derived from stearic acid residues.

3. A composition according to claim 1 wherein the R groups are derived from oils selected from the group consisting of soybean oil, canola, and cottonseed oil.

4. A composition according to claim 1 wherein the mixture contains up to about 40% LLS and LSL species.

* * * * *